US009884174B2

(12) United States Patent
Nebbia

(10) Patent No.: US 9,884,174 B2
(45) Date of Patent: Feb. 6, 2018

(54) MEDICAL DEVICE FOR DETECTION OF A LEAKAGE OF FLUID ON A SUBJECT

(71) Applicant: ELTEK S.p.A., Casale Monferrato (Alessandria) (IT)

(72) Inventor: Fabio Nebbia, Casale Monferrato (IT)

(73) Assignee: ELTEK S.P.A., Casale Monferrato (Alessandria) (IT)

( * ) Notice: Subject to any disclaimer, the term of this patent is extended or adjusted under 35 U.S.C. 154(b) by 10 days.

(21) Appl. No.: 14/900,937

(22) PCT Filed: Jun. 25, 2014

(86) PCT No.: PCT/IB2014/062594
§ 371 (c)(1),
(2) Date: Dec. 22, 2015

(87) PCT Pub. No.: WO2014/207676
PCT Pub. Date: Dec. 31, 2014

(65) Prior Publication Data
US 2016/0158517 A1 Jun. 9, 2016

(30) Foreign Application Priority Data
Jun. 26, 2013 (IT) .............................. TO2013A0523

(51) Int. Cl.
*A61M 39/02* (2006.01)
*A61B 5/02* (2006.01)
(Continued)

(52) U.S. Cl.
CPC .......... *A61M 39/02* (2013.01); *A61B 5/02042* (2013.01); *A61M 1/3656* (2014.02);
(Continued)

(58) Field of Classification Search
CPC ............ A61B 5/02042; A61M 1/3656; A61M 5/16836; A61M 39/02; A61M 5/158;
(Continued)

(56) References Cited

U.S. PATENT DOCUMENTS 6,947,131 B2 * 9/2005 O'Mahony ......... A61M 1/1692
210/96.2
8,376,978 B2 * 2/2013 Roger ................. A61M 1/3653
604/318

(Continued)

FOREIGN PATENT DOCUMENTS

JP 2007 178188 A 7/2007
JP 2008000218 A * 1/2008
(Continued)

OTHER PUBLICATIONS

International Search Report for International Application No. PCT/IB2014/062594, dated Sep. 17, 2014.

*Primary Examiner* — Sang Nguyen
(74) *Attorney, Agent, or Firm* — Heslin Rothenberg Farley & Mesiti P.C.; Victor A. Cardona, Esq.

(57) ABSTRACT

A medical device for detecting a leakage of fluid on a subject includes a support, configured for being secured on the subject, and an optical sensor on the support. The support defines, in a region between the optical sensor and a lower face thereof, a detection surface that can be reached by leakage fluid. The optical sensor is arranged for detecting a leakage of fluid. The optical sensor has a sensor body with an emitter and a receiver of electromagnetic radiation. The support and the sensor body have mutual-coupling means, for retaining the sensor body on the support in such a way that a presence of leakage fluid can be detected via the optical sensor.

19 Claims, 16 Drawing Sheets

(51) Int. Cl.
*A61M 1/36* (2006.01)
*A61M 5/158* (2006.01)
*A61M 5/168* (2006.01)

(52) U.S. Cl.
CPC ........ *A61M 5/158* (2013.01); *A61M 5/16836* (2013.01); *A61M 2005/1588* (2013.01); *A61M 2039/0229* (2013.01); *A61M 2205/15* (2013.01); *A61M 2205/3306* (2013.01)

(58) Field of Classification Search
CPC ...... A61M 2205/15; A61M 2205/3306; A61M 2039/0229; A61M 2005/1588
See application file for complete search history.

(56) References Cited

U.S. PATENT DOCUMENTS

| | | | | |
|---|---|---|---|---|
| 9,649,433 | B2* | 5/2017 | Lanier, Jr. | A61M 5/14224 |
| 2003/0210390 | A1* | 11/2003 | O'Mahony | A61M 1/1692 |
| | | | | 356/218 |
| 2004/0064046 | A1* | 4/2004 | Shehada | A61B 8/0825 |
| | | | | 600/437 |
| 2008/0195021 | A1* | 8/2008 | Roger | A61M 1/3653 |
| | | | | 604/4.01 |
| 2008/0249487 | A1* | 10/2008 | Engvall | A61F 13/0203 |
| | | | | 604/307 |
| 2009/0082649 | A1* | 3/2009 | Muller | A61M 1/3653 |
| | | | | 600/310 |
| 2009/0088612 | A1* | 4/2009 | Bouton | A61M 1/3653 |
| | | | | 600/309 |
| 2012/0139734 | A1* | 6/2012 | Olde | A61B 5/0416 |
| | | | | 340/605 |
| 2013/0109967 | A1* | 5/2013 | Park | H01L 31/16 |
| | | | | 600/432 |

FOREIGN PATENT DOCUMENTS

| | | |
|---|---|---|
| JP | 2008000219 A * | 1/2008 |
| WO | 01/68163 A2 | 9/2001 |
| WO | 2005/019416 A2 | 3/2005 |
| WO | 2006/001759 A1 | 1/2006 |
| WO | 2008/123814 A1 | 10/2008 |
| WO | 2009/038833 A1 | 3/2009 |

* cited by examiner

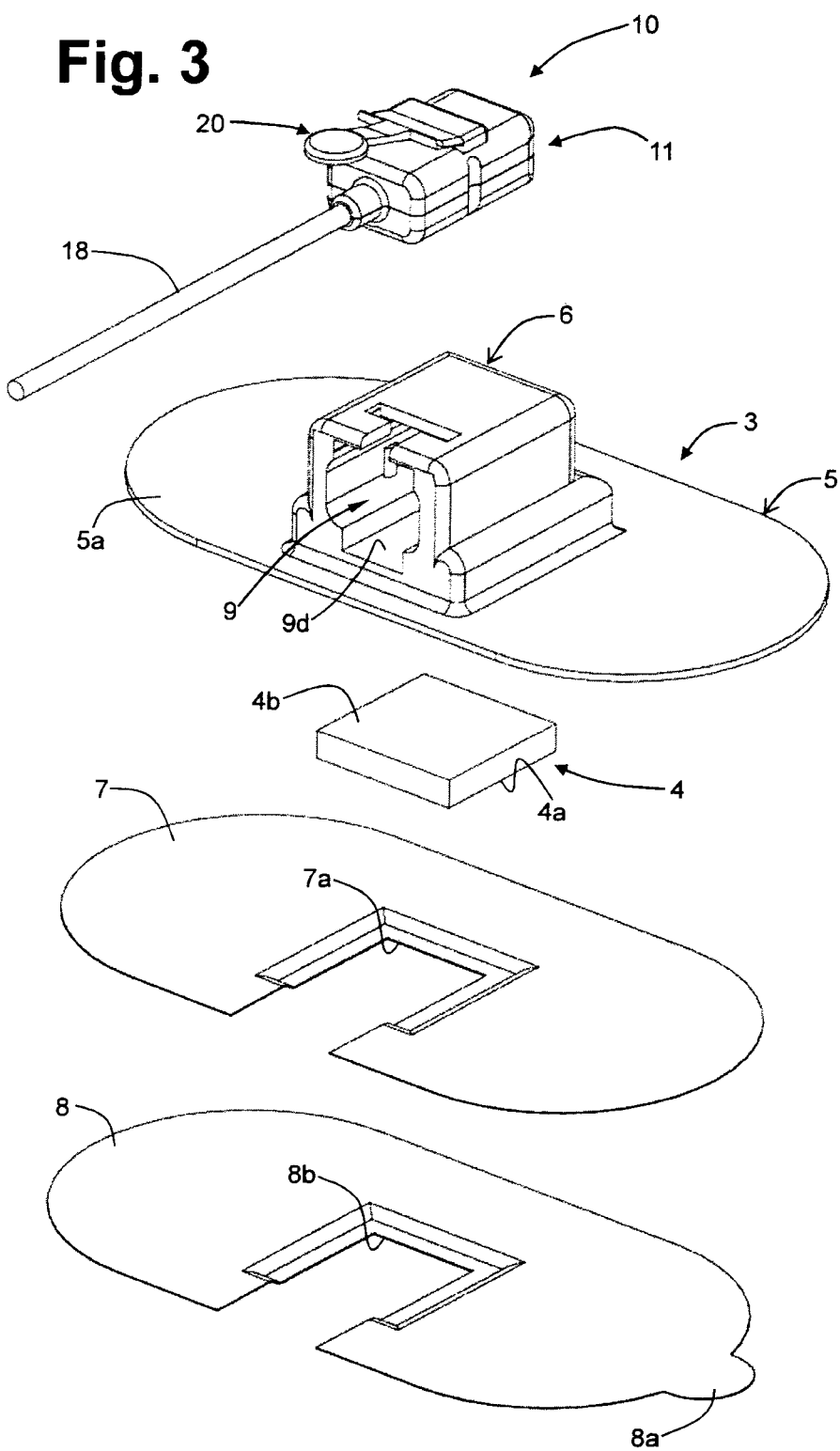

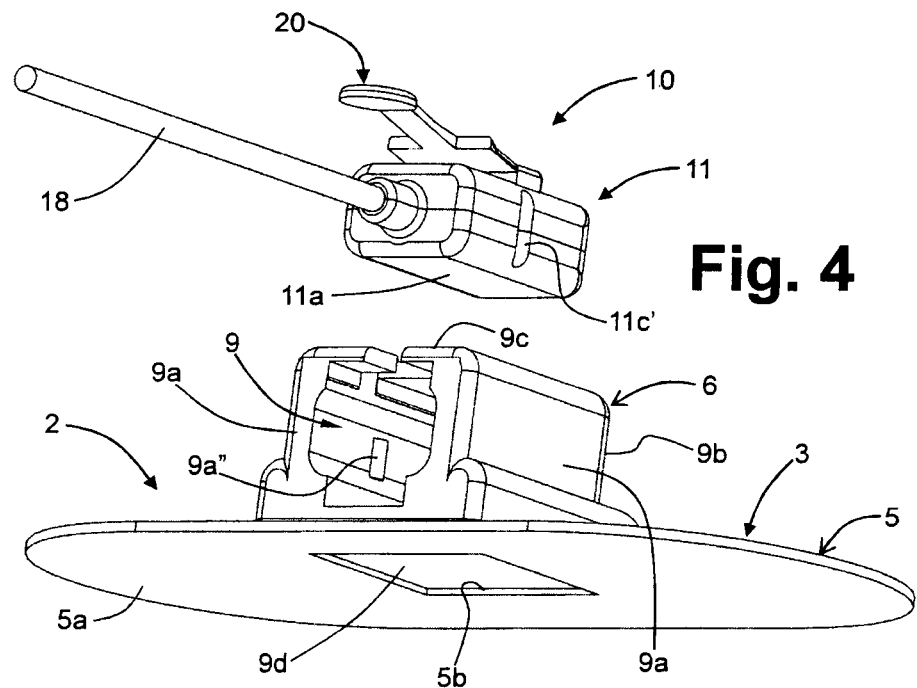
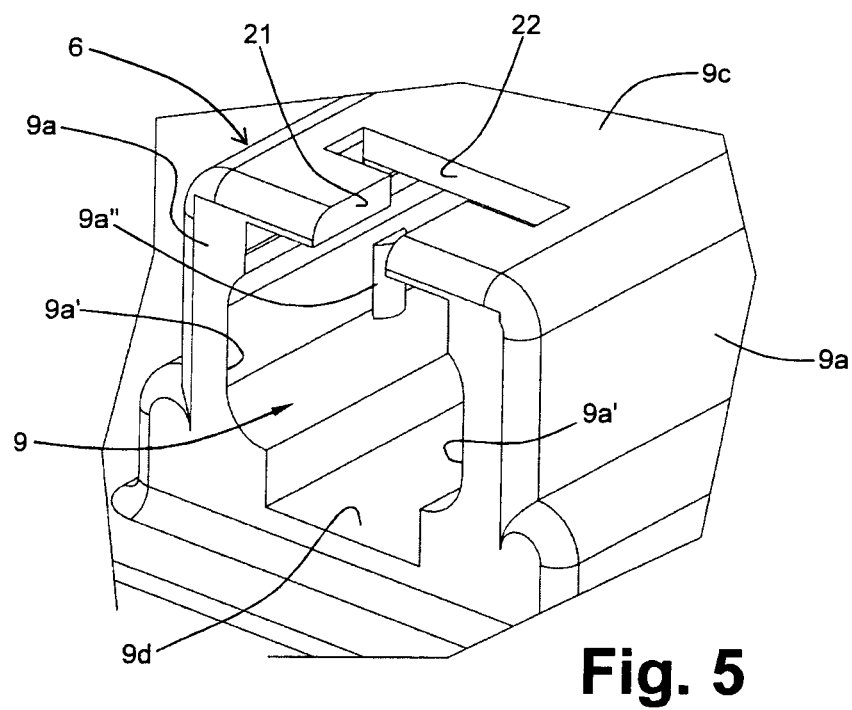

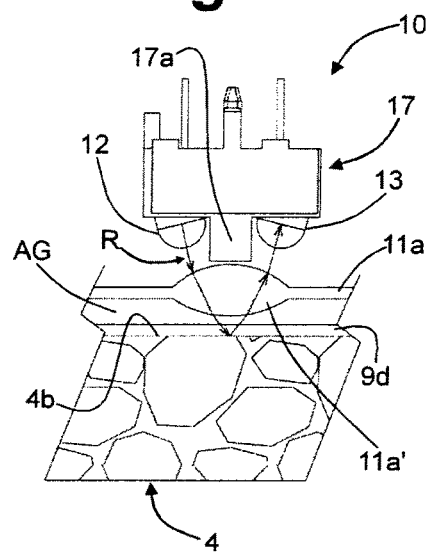
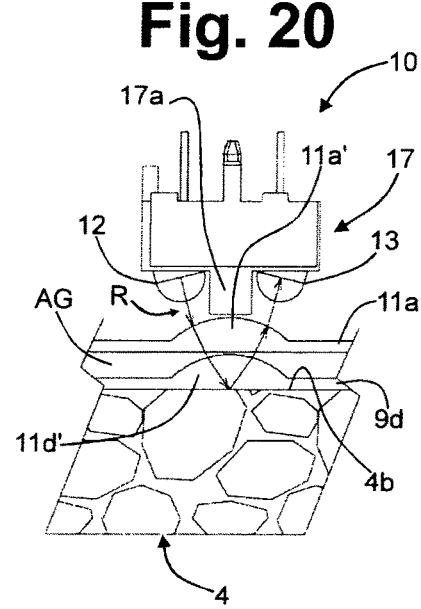
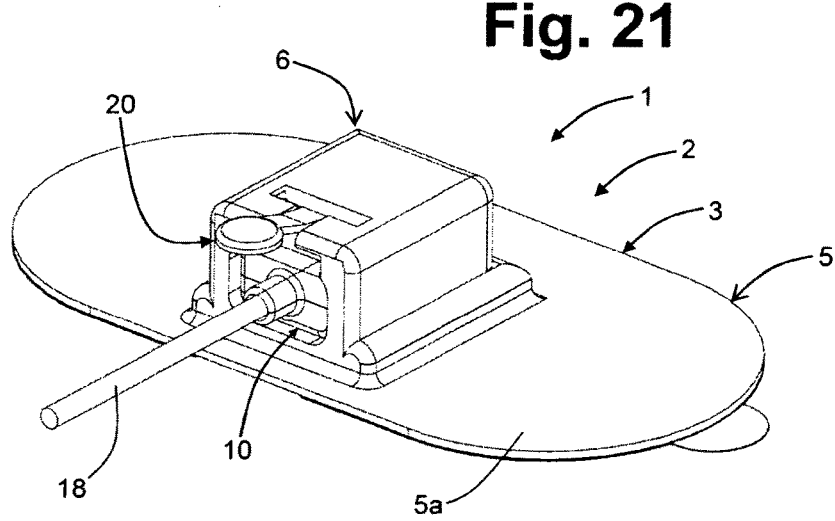

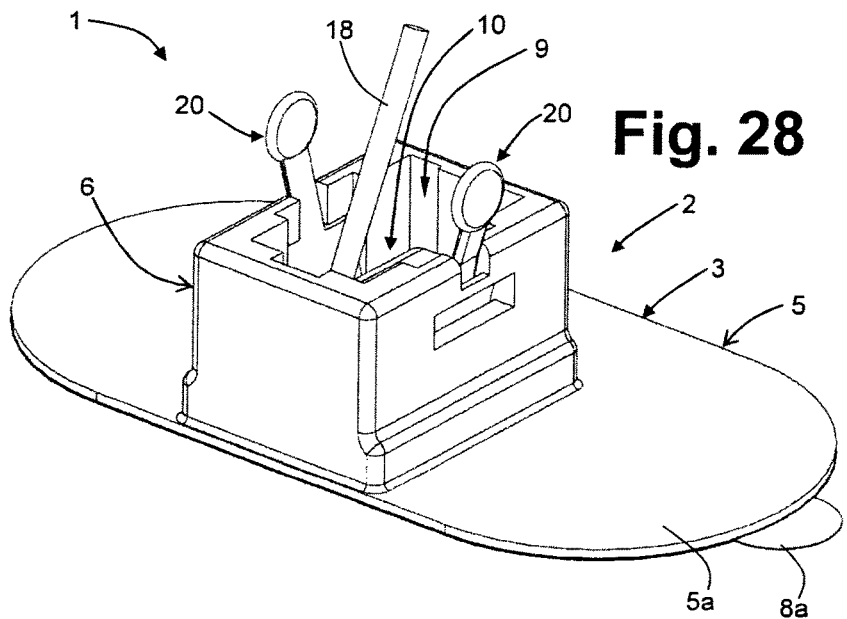
Fig. 28
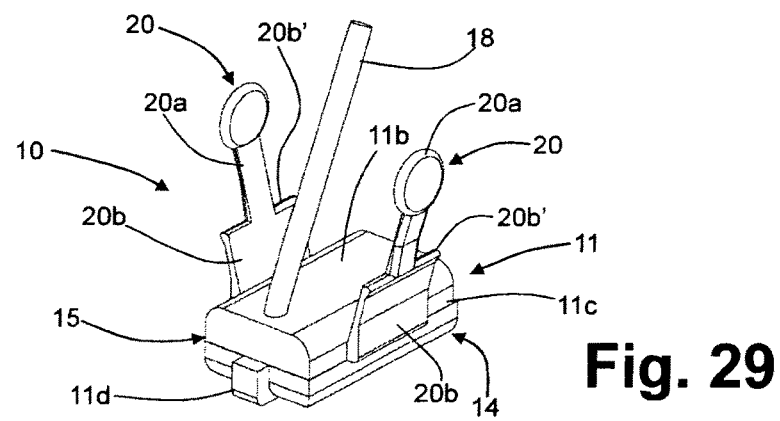
Fig. 29
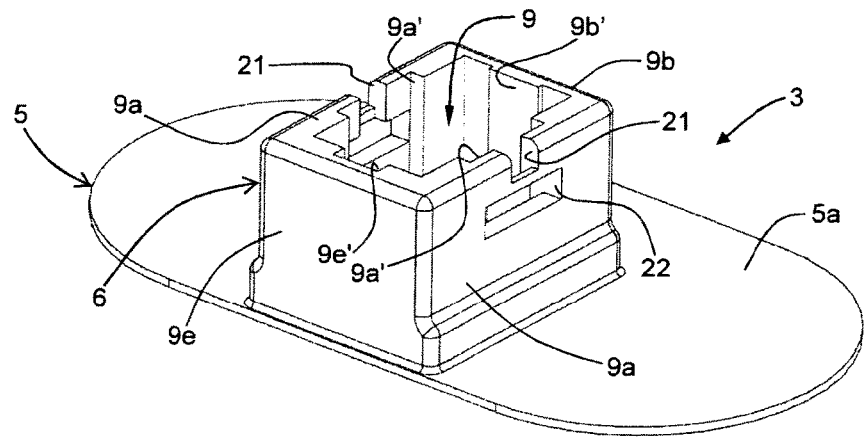

Fig. 30
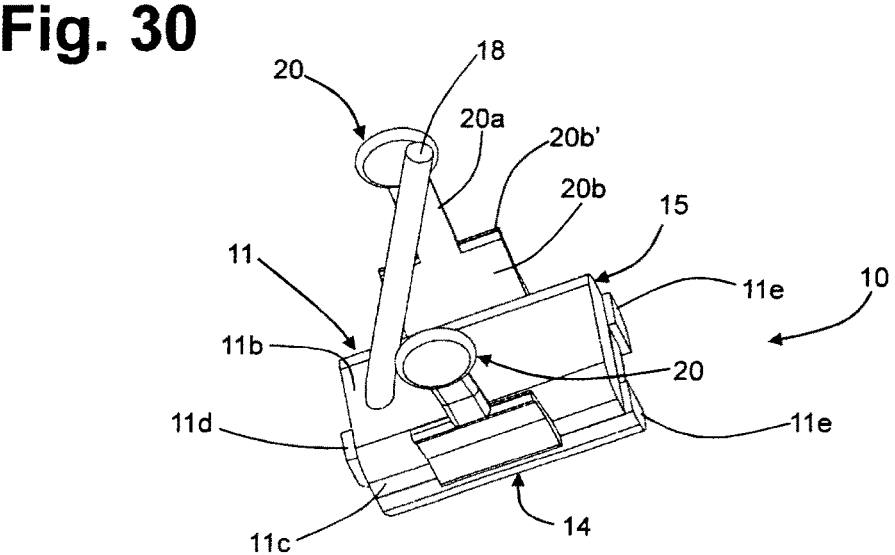
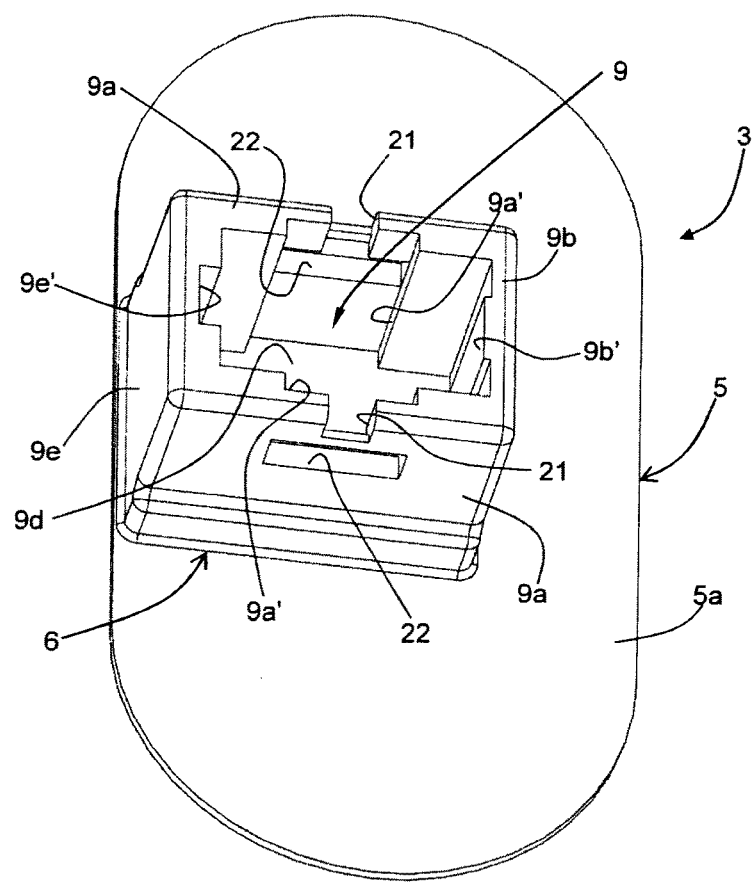

MEDICAL DEVICE FOR DETECTION OF A LEAKAGE OF FLUID ON A SUBJECT

CROSS REFERENCE TO RELATED APPLICATIONS

This application is a national stage filing under section 371 of International Application No. PCT/IB2014/062594, filed on Jun. 25, 2014, and published in English on Dec. 31, 2014, as WO 2014/207676 A1, and claims priority of Italian application No. TO2013A000523 filed on Jun. 26, 2013, the entire disclosure of these applications being hereby incorporated herein by reference.

FIELD OF THE INVENTION

The present invention relates to medical devices for detecting leakages of fluid on a patient, such as a biological or medical fluid, in particular leakages of blood or other fluid in an area of insertion of a needle or a cannula in the subject. The devices according to the invention find preferred application in the sector of control of treatments of haemodialysis, phleboclysis, and the like.

PRIOR ART

Medical devices of the type referred to above are, for example, used in combination with apparatuses for haemodialysis treatments. In these treatments, a cannula is inserted in the artery of a patient in such a way that a portion of the blood of the patient passes through a dialysis apparatus, where the blood undergoes purification. The purified blood is then re-introduced into the body of the patient via a second cannula, inserted in a vein of the patient. Treatments of this type are in general long, and it is not uncommon for the cannula, for example on account of a movement of the patient, to slide out accidentally from the corresponding wound made for insertion in the patient's skin, thus jeopardizing prosecution of the treatment. In the area of insertion of the cannulas plasters and/or bandages are in general applied on the skin of the patient, which have both the function of ensuring positioning of the cannula and the function of protecting the corresponding wound made for insertion in the patient's skin. Such plasters and/or bandages have, however, the consequence of concealing—and to a certain extent isolating—the area of insertion of the cannula through the skin, with the consequence that any accidental sliding-out of the cannula is frequently not detectable in a short time. Known devices of the type considered here have precisely the function of enabling detection in a short time of the presence of a leakage of liquid in the vicinity of the wound made for insertion of a cannula, which indicates a possible accidental sliding-out of the cannula itself from the skin of the patient, and consequently sets off an alarm.

A medical detection device of the type referred to above is known from the document No. WO 2006/001759A. The known device includes a plaster or tape compatible for medical purposes with a reinforcement made of polymeric material, which is associated underneath a layer of material designed to absorb fluids, and in particular a hydrophilic material that is able to absorb blood rapidly. The plaster is configured for temporary fixing on the skin of the subject, i.e., for the duration of the treatment, in the vicinity of the wound made for insertion of a cannula, in such a way that a lower surface of the absorbent layer directly faces the skin, in contact therewith. Inserted between the plaster and the skin of the subject, within the absorbent material, is a portion of an optical fibre, traversed in length by the light beam of a remote optical sensor, prearranged for detecting a leakage of blood following upon absorption of blood by the layer of absorbent material.

The devices that have such a structure are advantageous in so far as they enable constant, albeit indirect, monitoring of the condition of correct insertion of the cannula in an artery or vein of the patient. The presence of the absorbent layer, which operates basically as a sponge, enables timely detection of possible sliding-out of the cannula: in such an eventuality, in fact, the first leaked blood is rapidly absorbed by the absorbent layer and spreads equally rapidly within it so as to enable a timely detection by the optical sensor, thus triggering the alarm.

In the known solution mentioned, the sensor system is based upon the use of an optical fibre, an intermediate detection portion of which is curved through approximately 180°; i.e., it is substantially U-shaped. This U-shaped portion of the optical fibre is fastened via the plaster of the detection device and positioned in contact with the layer of absorbent material, in particular inserted within it, by providing a bushing for fastening the intermediate detection portion of the optical fibre in its curved configuration.

The optical fibre is relatively extensive, and typically reaches a device provided with an optical transmitter and a receiver and/or a monitoring apparatus, in any case a position that is remote with respect to the detection device applied to the patient. Associated to each of the two remote ends of the optical fibre are the aforesaid emitter and the aforesaid receiver of light radiation. The radiation generated by the emitter propagates within the optical fibre, starting from an end thereof, until it reaches the receiver at the opposite end of the optical fibre, substantially by internal reflection. In the absence of a leakage of blood, the peripheral wall of the optical fibre is in dry contact with the air and/or with the material constituting the absorbent layer so that the conduction of light along the entire optical fibre is not perturbed, with a constancy of signal detected by the receiver at the monitoring unit. On the other hand, following upon a leakage of blood absorbed by the layer of absorbent material, this blood comes into in contact with the wall of the optical fibre in the detection portion, thereby reducing substantially transport of light within the optical fibre: this occurs substantially on account of the modification of the characteristics of reflectance of the portion of the wall of the optical fibre that has come into contact with the blood, which is a medium having a refractive index higher than that of the material constituting the fibre itself. The reduced transmission of light thus induces a variation of the electrical signal generated by the receiver at the monitoring unit, which is considered as representing a leakage of blood, thereby triggering emission of the alarm.

The detection device known from the document No. WO2006/001759A proves effective for the purpose, in particular thanks to the use of a detection of an optical type that is generally more reliable than detection techniques of other types used in the sector (such as, detection based upon measurements of conductivity or capacitance). A drawback of the known solution, however, is the high cost of the detection device, principally caused by the use of an optical fibre. Also irrespective of considerations of cost, the fact that the optical fibre is relatively extensive in length may entail anomalous attenuation or perturbation of the light signal transmitted, regardless of the effective presence of a leakage of blood: for example, in the practical use of the device there may intervene phenomena such as to cause variation or attenuation of the light signal along the fibre, for example linked to deformations, curvatures, or undesirable twisting of the optical fibre, or else anomalous phenomena of refraction in other points, in particular along the remote or external portion of the fibre, for example if this is touched with wet or dirty hands.

In this regard, it should be noted that in the document No. WO2006/001759A part of the optical fibre, which here includes its U-shaped detection portion, is inserted in a structure owing to its compliant nature (the plaster and the absorbent layer) and hence is subject to deformation that may be transmitted to the optical fibre and that thus may potentially induce variations of the refraction/reflection of the optical signal in the fibre.

SUMMARY OF THE INVENTION

In its general terms, the object of the present invention is to provide a medical detection device of the type referred to at the start that is improved as regards its construction, which in particular is simple, inexpensive, and highly reliable.

The above and other objects still, which will emerge more clearly hereinafter, are achieved according to a preferential version of the present invention by a medical device for detecting a leakage of fluid on a subject, which has the characteristics referred to in the annexed claims. The invention likewise relates to an optical sensor, as well as to a support of a medical device for detecting a leakage of fluid on a subject.

In brief, a medical detection device as referred to at the start comprises a support, configured for being fastened temporarily on the patient, and an optical sensor provided on the support. The support defines, in a region comprised between a lower face thereof and the optical sensor, a detection surface that can be reached by leakage fluid, where the optical sensor is arranged for detecting a leakage of fluid following upon the presence of leakage fluid on at least part of the detection surface. The optical sensor includes an emitter and a receiver of electromagnetic radiation, both of which are associated to or housed in one and the same sensor body, which is fastened to the support of the device and is configured as a distinct or separate part with respect to the support itself. The support and the sensor body have mutual-coupling means, in particular for defining at least one predetermined position of retention of the sensor body on the support, where, in this predetermined position, the emitter and the receiver of electromagnetic radiation are oriented towards the detection surface, at a substantially predefined distance therefrom in such a way that a variation of an optical characteristic of the aforesaid detection surface, induced by the presence of leakage fluid, can be detected via the optical sensor.

Such a detection device according to the invention presents a simple and inexpensive construction and a high reliability. The emitter and the receiver of the optical sensor may advantageously be made up of electronic components of minimal cost, such as a light-emitting diode (LED) and a phototransistor, possibly integrated in one and the same electronic component, such as an opto-electronic component. Opto-electronic components of this type are commercially available at contained prices and have small overall dimensions, even less than 1 cm×1 cm×1 cm. In this way, the detection device has a clearly lower cost than a sensor based upon the use of optical fibre and, using a simple electric cable for transport of an electrical control signal to a monitoring unit, it is immune from problems linked to the need to prevent undesirable creasing or twisting or soiling of an optical fibre.

The fact that such an optical sensor is provided with a body of its own configured as a distinct part with respect to the support of the detection device enables production of the two parts (sensor and support) in distinct steps of the production process, it being possible to assemble these parts together subsequently, for example at the moment of effective use of the device on the subject: in this perspective, the solution according to the invention also makes it possible to subject the optical sensor and/or the support to a prior testing step, even before their mutual assembly.

The presence of the means for mutual coupling between the support and the sensor body enables determination of at least one predetermined position of fixing of the sensor on the support, which constitutes a further advantage in terms of simplicity of assembly and precision of operation of the device.

As will emerge more clearly hereinafter, in certain reflection optical sensors of the type that can be used for implementing the invention, it is important to position the emitter and the receiver with extreme precision with respect to a reflection surface, in view of the focal distances involved, and this need is satisfied by the presence of the aforesaid mutual-coupling means.

In one embodiment, the support comprises at least one from among:
- a fluid-absorbing element, set in such a way that the lower face of the support includes a lower surface of the fluid-absorbing element, with the optical sensor that is arranged for detecting a leakage of fluid following upon absorption of leakage fluid by the fluid-absorbing element as far as an upper surface thereof;
- a wall that is at least in part transparent to electromagnetic radiation and has a lower surface that extends at least in part in the aforesaid region comprised between the optical sensor and the lower face of the support; and
- a detection surface, which comprises at least one between an upper surface of a fluid-absorbing element, such as the one just referred to, and a lower surface of a wall of the support that is transparent to electromagnetic radiation, such as the one just referred to.

The use of an absorbent element of the type referred to above presents the advantage of enabling a rapid absorption of the leakage fluid—and of containing to a certain extent the diffusion thereof on the subject—and hence a rapid detection on the basis of the variation of an optical characteristic of a surface thereof that the optical sensor faces. On the other hand, as will be seen, the device according to the invention may also be used in the absence of an absorbent element of this sort, in which case the detection surface may be advantageously constituted by the aforesaid transparent wall of the support, which the optical sensor faces. The absorbent element and the aforesaid transparent wall may coexist in various embodiments, as exemplified hereinafter, in which case the detection surface may basically be at the interface between the absorbent element and the transparent wall.

The body of the aforesaid transparent wall is hence set between the detection surface and the sensor body and/or the receiver and the emitter. In this way, the optical sensor is in a further protected position and is set at a distance from the detection surface, which by its nature and function is can be reached by contaminating substances, such as the blood of a patient.

In one embodiment, the support comprises a supporting body having a receiving seat that identifies the predetermined position of the sensor body, and the mutual-coupling means are configured for positioning and retention of the sensor body in the receiving seat.

In this way, a body of the support—to which there may possibly be associated components additional to the optical sensor and to an absorbent element—includes a specific seat for the sensor body—which also identifies the aforesaid predetermined position. In such an embodiment, the mutual-coupling means are configured for guaranteeing precise positioning of the sensor body in the predetermined position identified by the receiving seat, in which the emitter and the receiver are located at a substantially predefined distance from the detection surface. The mutual-coupling means likewise enable the sensor body to be withheld with extreme precision in the aforesaid seat, which is preferentially configured for providing itself a sort of peripheral protection for the sensor body.

In one embodiment, the sensor body comprises a sensor casing, positioned within which are the emitter and the receiver, with the latter that preferably face a wall of the sensor casing that is transparent to electromagnetic radiation and faces the detection surface.

In this way, the emitter and the receiver of electromagnetic radiation are, if required, completely housed within the sensor casing (even though an embodiment is not excluded in which an active optical part of the emitter and the receiver projects or gives out onto the outside of the sensor body or casing) and face a wall of the casing itself that is transparent to electromagnetic radiation and faces the detection surface, when the sensor casing is in its predetermined position or within the retention seat.

An embodiment of the above sort guarantees a high degree of protection of the most sensitive and costly parts of the device, represented by the emitter and the receiver of the optical sensor, for example for the purpose of a corresponding re-use. With such an embodiment, moreover, the sensor casing, and hence the emitter and the receiver mounted therein, are at a distance from the detection surface, with the casing itself that bestows a further characteristic of protection of the optical sensor, preventing any possible direct contamination thereof, for example by leaked blood.

In one embodiment, in the predetermined position of the optical sensor, a wall of its body or casing that is at least in part transparent to electromagnetic radiation faces a wall of the support that is at least in part transparent to electromagnetic radiation, in particular in the aforesaid predetermined position or at the aforesaid receiving seat, the two walls being preferably but not necessarily separated from one another by an air gap. The presence of the aforesaid walls that are at least in part transparent affords a maximum degree of protection of the emitter and the receiver elements, as well as optimizing, if so required, operation of the optical system.

In a preferred embodiment, the mutual-coupling means are releasable or separable coupling means, configured for enabling removal of the sensor body or casing from the aforesaid predetermined position or its extraction from the corresponding retention seat.

As already explained, the fact that the sensor body or casing is configured as a distinct part from the support facilitates production of the two parts in distinct steps of the manufacturing process, their possible separate storage and their subsequent coupling when required, as well as prior testing of the optical sensor and/or of the support separately. The fact that the coupling means are releasable enables, when required, simple separation of the sensor from the support, for example when one of the two parts is unusable for any reason (consider, for example, any accidental dropping of the device, with its surface that is designed to rest on the skin coming into contact with a potentially contaminated floor, or again any accidental disconnection of the optical sensor from a cable thereof for transport of the electrical signal).

In this perspective, in a particularly advantageous embodiment, the optical sensor represents a reusable element or component of the detection device, whereas the support is a disposable element or component thereof. In this way, as may be appreciated, the advantages of an economic nature offered by the solution according to the invention are further increased, above all when it is considered that known devices, for example of the type described in the document No. WO2006/001759, are basically disposable devices.

In one embodiment, a body of the support defines at least one from among:
  two opposite side walls of a receiving seat, between which the sensor body or casing can be positioned, in particular by being slid therein;
  an end wall and two side walls of a receiving seat, between which the sensor body or casing can be positioned, the end wall being preferably perpendicular to the side walls; and
  an opening for insertion of the sensor body or casing in a receiving seat for the sensor casing, the opening for insertion being generally opposite to an end wall of the receiving seat.

Thanks to the above characteristics, which can be implemented separately or alternatively or in combination, the support includes a seat that encloses and protects the body or the casing of the sensor—to a greater or lesser extent according to the type of embodiment—, at the same time identifying the aforesaid predetermined position and facilitating and rendering intuitive assembly of the two parts in question.

In one embodiment, it is preferable for at least two opposite walls of a receiving seat that identifies the predetermined position for the sensor to have a shaped or irregular inner-surface profile substantially complementary to an outer-surface profile of two corresponding opposite side walls of the sensor body or casing, albeit with slight dimensional differences that enable a mutual guided sliding thereof. In this way, in addition to enabling insertion and precise positioning of the sensor with respect to the support, the risks of wrong insertion of the sensor itself in the corresponding receiving seat can be reduced.

In one embodiment, the mutual-coupling means between the support and the sensor casing comprise at least one from among:
  a releasable engagement device, including at least one engagement element on one between the sensor casing and the support and at least one corresponding retention element on the other between the sensor casing and the support, where at least one between the engagement element and the retention element preferably includes at least one from among a seat, a relief, and an elastically deformable part, which is made integrally with the sensor body or casing or with a body of the support;
  sliding and/or positioning guides, which include at least one guide element on the support and at least one corresponding guided element on the sensor body or casing;

positioning elements, which include at least one first part of one between the sensor body or casing and the support, and at least one second part of the other between the sensor body or casing and the support, the at least one first part and the at least one second part co-operating for defining a predetermined retention position;

at least one surface in relief of one between the sensor body or casing and the support and at least one corresponding recess or seat of the other between the sensor body or casing and the support, and the at least one relief and the at least one recess or seat being coupleable, preferably engageable, with one another and releasable from one another, following upon positioning, respectively removal, of the sensor body or casing with respect to its predetermined position or with respect to a receiving seat thereof; and a combination keying, for exclusive coupling and/or positioning of the sensor body or casing with respect to its predetermined position on the support or in its seat on the support, where the key includes at least one first key element on the sensor body or casing and at least one second key element on the support, which co-operate with one another uniquely, where said key elements preferably include a relief and a seat or cavity.

The above characteristics, which can be implemented in isolation or in combination or as alternatives, enable a further enhancement of the advantages of the invention. The presence of a releasable engagement element proves very useful when it is necessary to separate the optical sensor from the support, for example when the latter is understood as being a part that is disposable after use. The presence of guides facilitates insertion, positioning, and possible removal of the sensor body or casing with respect to its predetermined position on the support or with respect to its receiving seat. The presence of a positioning element may likewise enable a precise axial and/or angular position of the optical sensor with respect to the support to be reached and maintained, when the latter is envisaged, improving the respective optical coupling. Surface reliefs and slots can themselves function as a releasable engagement device, for example substantially a snap-action device, as well as functioning as insertion/sliding/positioning guides and as unique coupling and/or positioning keys between the sensor body or casing and the support.

The presence of a coupling and/or positioning key preferably ensures a unique coupling and/or a positioning between the sensor body or casing and the support in the corresponding predetermined position or receiving seat, thereby eliminating the risks of wrong assembly between the two main parts of the detection device (for example, preventing the risk of assembly between a first type of optical sensor and a different support prearranged for other similar optical sensor, or else preventing a risk of assembly of the optical sensor on the support in a rotated or in any case incorrect position).

In one embodiment, the sensor casing comprises, or has associated to it, at least one element that can be gripped, to facilitate removal of the sensor casing from the predetermined position or its extraction from the receiving seat. Very preferably, the aforesaid element that can be gripped belongs to a releasable engagement device, provided between the sensor casing and the support.

In one embodiment, the support has a body with a base, preferably at least in part substantially laminar, and an upper body part that rises from the base and in which the receiving seat for the optical sensor is defined, the base and the upper body part being preferably made of a single piece of synthetic material or of a polymeric material.

In this way, one and the same body of the support—to which there may possibly be associated components additional to the sensor and to an absorbent element—includes both a specific seat for the sensor and a corresponding base portion—possibly including the absorbent element—to be rested on the patient.

In one embodiment, the support has a body with a lower cavity, where:

the bottom of said cavity is defined by the lower surface of the aforesaid wall of the support that is at least in part transparent to electromagnetic radiation, and/or housed at least in part in the cavity is the fluid-absorbing element, with the corresponding upper surface that is substantially in contact with the lower surface of the wall of the support, which is at least in part transparent to electromagnetic radiation.

The aforesaid cavity of the supporting body advantageously provides a sort of chamber for collecting leakage fluid, for the purposes of the detection performed by the sensor. When the device includes an absorbent element, this can be housed at least in part in the cavity, with the upper surface thereof facing the optical sensor, with the cavity that thus operates also as positioning element for the absorbent element. When the device does not include an absorbent element, the leakage fluid can directly reach the inside of the cavity as far as the detection surface, which forms the bottom of the cavity itself.

In one embodiment, the supporting body and the fluid-absorbing element are mutually constrained, with the fluid-absorbing element that itself forms at least part of a base of the support, to the advantage of simplicity of production of the device.

At least one portion of the body of the support may conveniently be made of a single piece, for example via moulding of a synthetic material, such as a polymer or an elastomer or a resin, in particular for integrating directly both a substantial part of a resting base and the upper part that identifies the seat or predetermined position for the sensor casing, for example defined by the aforesaid receiving seat. Next, in a readily automatable way, in a position corresponding to the resting base and/or the corresponding laminar portion, there may be applied underneath the layer of absorbent material, for example engaged or glued, possibly fixed by the retention strip, which may be adhesive or bi-adhesive. It should, however, be noted that, according to possible less advantageous variant embodiments, the resting base or the corresponding laminar portion and the upper part of the aforesaid body of the support may also be configured as distinct parts rendered fixed with respect to one another (for example, glued or welded), before or after association of the layer of absorbent material to the base.

BRIEF DESCRIPTION OF THE DRAWINGS

Further purposes, characteristics and advantages of the present invention emerge clearly from the ensuing detailed description, with reference to the annexed schematic drawings, which are provided purely by way of non-limiting example and in which:

FIG. 3 is a partially exploded view of the device of FIGS. 1 and 2;

FIG. 4 is a perspective view of an optical sensor and of a supporting body of a detection device according to the invention;

FIG. 5 is a perspective view of a detail of the aforesaid supporting body;

FIGS. 19 and 20 are schematic representations, similar to those of FIGS. 16 and 17, of possible variant embodiments of the invention;

FIG. 21 is a perspective view of a medical detection device according to a further embodiment of the invention;

FIG. 28 is a perspective view of a medical detection device according to a further embodiment of the invention;

FIGS. 29 and 30 are perspective views, according to different angles, of an optical sensor and a supporting body of the device of FIG. 28;

DESCRIPTION OF PREFERRED EMBODIMENTS OF THE INVENTION

The reference to "an embodiment" or "one embodiment" that may be present in various points of this description is intended to indicate that a particular configuration, structure, or characteristic described in relation to the embodiment is comprised in at least one embodiment. Hence, phrases such as "in an embodiment" or "in one embodiment" and the like that may be present in various points of this description do not necessarily refer to one and the same embodiment. Furthermore, particular conformations, structures, or characteristics may be combined in any adequate way in one or more embodiments, even different from the ones represented. The references used herein are provided merely for convenience and hence do not define the sphere of protection or the scope of the embodiments.

Figure 1:
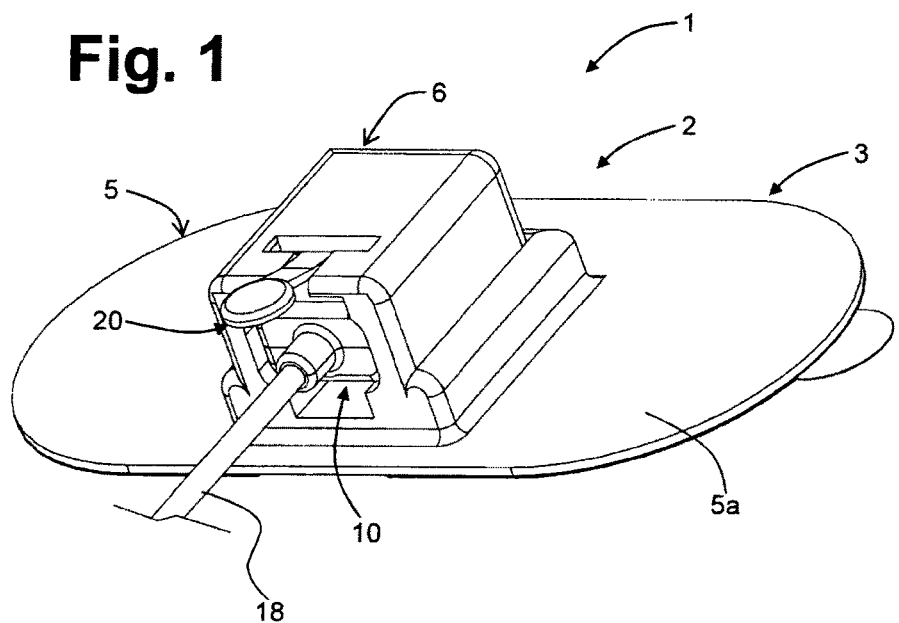
FIGS. 1 and 2 are perspective views, according to different angles, of a medical detection device according to the present invention.
Figure 2:
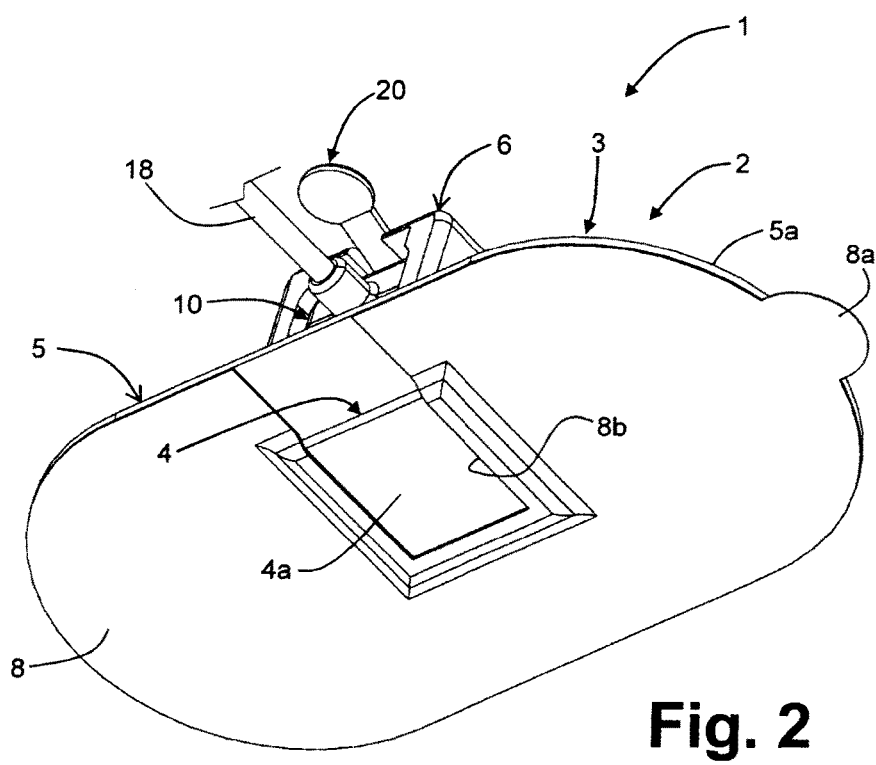

With initial reference to FIGS. 1-3, designated as a whole by 1 is a medical device for detecting a leakage of fluid on a subject, such as a biological or medical fluid. By way of preferential example, the device 1 is conceived for detecting a leakage fluid in the vicinity of a wound of the skin of a patient, such as for example a leakage of fluid substantially in a position corresponding to a wound caused by insertion of a cannula (or needle) in the body of the patient. The device 1 finds a preferred application in the sector of control of treatments of haemodialysis, phleboclysis, and the like, as referred to in the introductory part of the present description, and in this perspective the leakage fluid may be blood that comes out of an aforesaid wound, on account of accidental sliding-out of a sampling cannula. Once again with reference to the case of haemodialysis, the leakage fluid may also be blood that comes out of a cannula used for re-introducing into a vein of the patient purified blood following upon haemodialysis, in the event of accidental sliding-out of the cannula from the corresponding wound made for insertion thereof in the skin. The detection device according to the invention may be used also in other medical environments, such as for example the aforesaid monitoring of the condition of a needle or a cannula for infusion of blood or phleboclysis of medical substances into a patient (for example, for intravenous therapy), for monitoring possible leakages of blood or excretions from skin wounds of a patient, not necessarily caused by a needle or a cannula, or once again for monitoring possible impregnation of bandages or pads associated to the body of a patient with biological or medical fluids.

It will thus be appreciated that the expression "leakage of fluid on a subject" that may be present in various points of this description and in the claims is intended to comprise a variety of cases, such as the ones exemplified above, and more in general both the leakage of a biological fluid from the body of a patient and the leakage of a fluid, such as a medical fluid or a biological fluid, from a device intended for infusion of a fluid into the body of a patient or intended for sampling of a fluid from the body of the patient or intended for retention of a fluid on the patient. It will likewise be appreciated that, for some of the applications mentioned, the device according to the invention does not necessarily have to be in direct contact with the skin of a patient, even though this is preferable, for example at least in the aforesaid cases of haemodialysis and phleboclysis.

The device 1 comprises a support 2, which includes a supporting body designated as a whole by 3. In various embodiments, such as the one exemplified, the support 2 comprises or has associated at least one layer of fluid-absorbing material, which is designated as a whole by 4, here having a generally parallelepipedal configuration, and is referred to hereinafter for simplicity also as "absorbent layer" or "layer". The absorbent layer 4 may be of any type known in the specific sector and may, for example, consist of a fabric (here including a non-woven fabric), a sponge, a paper material or some other material distinguished by an adequate degree of hydrophilicity.

The support 2 is configured for temporary fixing on a patient, for example on a wound caused by a cannula, in such a way that a lower surface of the layer 4, designated by 4a in FIG. 2, can face the skin of the subject, for example be in direct contact therewith or even just in the proximity of the skin (as has been said, on the other hand, in various applications the device does not need to be in direct contact with the skin). The layer 4 preferably has a relatively small thickness, for example comprised between 0.1 mm and 8 mm, preferably between 0.5 and 3 mm.

The device 1 further comprises an optical sensor, designated as a whole by 10, which is designed to detect a leakage of fluid following upon absorption of leakage fluid by the layer 4.

As explained previously, according to a characteristic of the invention, the optical sensor 10 comprises an emitter and a receiver of electromagnetic radiation or of an opto-electronic type, described hereinafter, which are preferably fastened to a sensor body, where the aforesaid sensor body 10 is in turn fastened to the body 3 of the support 2 and is configured as a distinct part with respect thereto. In what follows, for simplicity reference will be made to the case of a sensor body that is configured as a casing within which the aforesaid the emitter and receiver are mounted, taking, however, for granted that in embodiments different from the ones illustrated the sensor body may include a support (see, for example, the component designated hereinafter by 17) to which the emitter and the receiver are fastened and are at least in part directly exposed, i.e., not enclosed in one and the same casing. Once again, the sensor body can include a prevalently closed casing having in a wall thereof at least one discontinuity (for example, a through opening) located in a position corresponding to which are the active optical parts of the emitter and receiver. In the figures, the body configured as sensor casing is designated as a whole by 11.

In the embodiment represented, the lower face of the support 2, visible as a whole in FIG. 2, includes at least one portion of the lower surface 4a of the layer 4: in this way, during use of the device 1, the lower surface 4a can directly face the skin of a subject, preferably in contact therewith. For this purpose, in the example illustrated, the body 3 has a resting and/or fixing base 5, and an upper part 6 that rises from the base 5, where the base and upper part are preferably (but not necessarily) made of a single piece, for example via moulding of at least one synthetic material or a polymer, for example a silicone, a PVC (polyvinyl chloride), a TPE (thermoplastic elastomer), a TPU (thermoplastic polyurethane), etc. Preferentially, an elastomer or some other material similar to rubber is chosen, or a foamed material, such as an elastic and/or soft material. In this perspective, the acronym TPE is meant to designate also a particular family of materials which have characteristics similar to rubber, comprising TPSs (or TPE-Ss, block copolymers based on styrene), TPOs (or TPE-Os, Thermoplastic Polyolefins), TPVs (or TPE-Vs, Thermoplastic Vulcanizates), such as mixtures of resins of polypropylene (PP), polyethylene (PE), and rubber EPDM. The base 5 and the upper part 6 may also be made as parts distinct from one another associated or fixed together.

Associated underneath the base 5 is the layer of absorbent material 4, so that at least one portion thereof is located in a position corresponding to the upper part 6, the latter being shaped to define at least one predetermined position of retention of the sensor 10, i.e., of its body or casing 11. As clarified hereinafter, the aforesaid predetermined position is preferentially identified by a seat for receiving the casing 11, which is directly defined in the part 6 of the body 3.

In one embodiment, such as the one represented, the base 5 of the body 3 comprises a laminar portion 5a, i.e., a portion of a relatively small thickness (for example, comprised between 0.1 mm and 1 mm) and hence relatively flexible so that it can at least in part adapt to the profile of a part of the body of the patient on which the device 1 can be applied (for example, an arm or a leg). With reference to the example illustrated, the laminar portion 5a has a generally oblong shape, substantially like a large plaster, for example having a width of 10 mm and a length of 80 mm, with the upper part 6 that rises from an intermediate area of the portion 5a.

As has been said, in a preferred embodiment, the body 3 is made of a single piece of just one material. For instance, the body 3 may be made of an elastomer, such as silicone, and be relatively flexible in the thin parts, here represented by the laminar portion 5a, and instead stiffer in the thicker parts, here represented by the upper part 6, which identifies the predetermined position for the sensor 10. In other embodiments, on the other hand, the body 3 may be made of two co-moulded or over-moulded thermoplastic materials, for instance, a first body part of moulded thermoplastic material that is substantially stiff (comprising the upper part 6), co-moulded with or over-moulded on which is a second body part (including the base 5) made of more flexible and/or elastic material, such as an elastomer having characteristics of chemical compatibility and/or good adhesion with the other stiffer material. Preferably, the aforesaid first and second body parts comprise a substantially in common thermoplastic material, designed to determine the aforesaid chemical compatibility and/or good mutual adhesion. For example, in one embodiment, the first substantially stiff part comprises polypropylene (PP) and/or polyethylene (PE), whereas the second part made of more flexible material comprises a mixture of polypropylene (PP) and/or polyethylene (PE) and EPDM rubber.

In the non-limiting example illustrated, applied underneath the laminar portion 5a is a retention strip or film, designated by 7 in FIG. 3, made, for example, of a flexible synthetic material and having at least one respective face that is adhesive or rendered adhesive; preferably, the strip 7 is bi-adhesive, i.e., both of its major faces are adhesive or rendered such. As may be noted, in FIG. 3 the retention strip 7, which may have a peripheral profile generally corresponding to that of the portion 5a of the body 3, is applied underneath the portion 5a of the body 3, with the absorbent layer 4 at least in part set in between. The strip 7 is not in any case a basic element of the invention, and may possibly even be absent, with the layer 4 fastened to the body of the support 2 in some other way.

In the example, the strip 7 has an opening, at least one region 7a of which extends substantially in a region corresponding to the upper part 6 of the body 3 in such a way that at least one portion of the lower surface 4a of the layer 4 can be set, in use, on the skin of the patient, at least in a position corresponding to the aforesaid region 7a. From FIG. 4 it may hence be seen how, in a preferred embodiment, at least partially defined in the body 3, in particular in its base 5, is a lower seat or cavity 5b, within which the absorbent layer 4 can at least be partially housed in order to enable precise positioning thereof. The bottom of the seat 5b is located substantially in a position corresponding to the upper part 6 of the body 3 and, as will be seen, is defined by a material transparent to electromagnetic radiation generated by the emitter of the optical sensor 10. The seat 5b may possibly also be defined at least partially in a position corresponding to a bottom present in the upper part 6.

Preferentially, the thickness of the layer 4 is greater than the depth of the corresponding seat 5*b* so that the layer 4 projects slightly downwards with respect to the lower surface of the base 5, also such that it can be at least slightly compressed during application on the subject. In this way, moreover, following upon application of the retention strip 7, the upper surface of the layer 4 is well positioned and/or in contact with the bottom of the seat 5*b*.

Once again with reference to the non-limiting example referred to in FIG. 3, preferentially applied to the lower face of the strip 7 is a further peelable sealing strip or film, designated by 8, which coats the lower surface of the strip 7, which has preferably but not necessarily a surface that is adhesive or rendered such. The function of the peelable strip 8 is basically that of protecting the lower surface of the retention strip 7 until effective use of the device 1. When the latter has to be applied on the skin of a patient, the strip 8 can be removed, for example by pulling on a tab 8*a* thereof in order to leave directly exposed the lower face of the support 2—including the lower surfaces of the layer 4 and of the strip 7—, which can then be made to adhere to the skin of the patient.

In the example illustrated in the figures, and as may be appreciated in particular in FIG. 3, the sealing strip 8 has an opening 8*b* having a profile corresponding to that of the opening 7*a* of the strip 7. The presence of the opening 8*b* is not indispensable, in view of the possibility of removal of the strip 8. Instead, the opening 8*a* may be omitted in the case where it is desired to protect also the lower surface 4*a* of the layer 4 via the strip 8.

According to a further characteristic of the invention, the support 2 and the sensor body, here represented by the casing 11, have mutual-coupling means, for defining at least the aforesaid predetermined position of retention of the casing 11 on the support 2. In this predetermined position, the emitter and the receiver of the sensor 10 face a detection surface, which can be reached by leakage fluid, at a substantially predefined distance from this surface. The latter detection surface is located in a region of the support 2 that is comprised between the optical sensor 10 and the lower face of the support itself and, as will appear more clearly hereinafter, comprises at least one from between the upper surface of the layer 4 and the bottom surface of the seat 5*b*, and in this perspective the emitter and the receiver of the sensor 10 are in a substantially predefined position with respect to the layer 4 and/or to the aforesaid bottom surface of the seat 5*b*.

Clearly visible in FIGS. 4 and 5 is the upper part 6 of the support 2, and in particular of its body 3. In a preferred embodiment, such as the one exemplified, the aforesaid part 6 defines at least the receiving seat mentioned previously, designated as a whole by 9, which identifies at least the predetermined position of retention of the sensor casing 11. In what follows, preferred embodiments of the seat 9 will be described, but it should be considered that the seat 9 could be differently shaped, albeit maintaining its function of identifying at least the predetermined position of retention of the sensor casing 11.

In general terms, the receiving seat 9 comprises at least two opposite side walls, designated by 9*a*, which rise from the base 5, between which the sensor casing can be inserted. In the case exemplified, the seat 9 moreover includes at least one end or rear wall, which also rises from the base 5 and is generally perpendicular and contiguous to the side walls 9*a*; the aforesaid rear wall—albeit not directly visible in so far as it is set on the back of the part 5—is designated by 9*b* in FIG. 4.

In the preferred embodiment exemplified, the receiving seat 9 further comprises an upper wall 9*c*, which extends between the side walls 9*a* and is generally opposite to a lower wall 9*d*, which in practice forms also the bottom of the lower seat 5*b* for the absorbent layer 4 (see FIG. 4). In an embodiment of this type, the receiving seat 9 has an opening or front mouth, not identified but clearly visible in FIG. 5, for insertion into the seat itself of the sensor 10, i.e., of its casing 11. In such an embodiment, the walls 9*a*-9*d* that delimit the seat 9 gird the casing 11 on a number of sides so as to provide also a sort of protective chamber thereof. In a possible variant embodiment, described hereinafter, the mouth for insertion of the casing 11 in a corresponding receiving seat is defined in a position corresponding to the upper end of the part 6 of the body 3.

As has been mentioned, in one embodiment, the supporting body 3 has at least one wall, which is made at least in part of a material that is transparent to electromagnetic radiation generated by the emitter of the optical sensor 10, this wall being here represented by the wall designated by 9*d*, which is operatively set between the body of the sensor 10, here represented by the casing 11, and the upper surface of the layer of absorbent material 4. For this purpose, preferably the entire supporting body 3 is made of a material transparent to the aforesaid radiation, even though not excluded from the scope of the invention is formation of the body 2 using a number of materials, at least one of which is transparent to electromagnetic radiation in the position envisaged for the sensor casing 11, here identified by the seat 9 (the lower wall 9*c* of which, as has been said, is made of a material transparent to electromagnetic radiation).

For instance, in one embodiment, the body 3 includes a plate of a material transparent to electromagnetic radiation, which forms the wall 9*d*, over-moulded on or co-moulded with which is the rest of the body 3, made of a material not transparent to the radiation. Indicatively, the thickness of the wall 9*d*, in its part traversed by radiation, may be comprised between 0.5 and 4 mm.

Of course, the material that, in various points of this description and of the claims, is defined as "transparent to electromagnetic radiation" may be a transparent material in a broad sense, i.e., one that can be traversed by visible light (even though, in other embodiments, the transparency may refer also to non-visible wavelengths), and the electromagnetic radiation generated by the emitter 12 may be a radiation of visible light.

FIGS. 6-9 show, in different views, the opto-electronic or electromagnetic sensor 10 used in a preferred embodiment of the invention.

Figure 9:
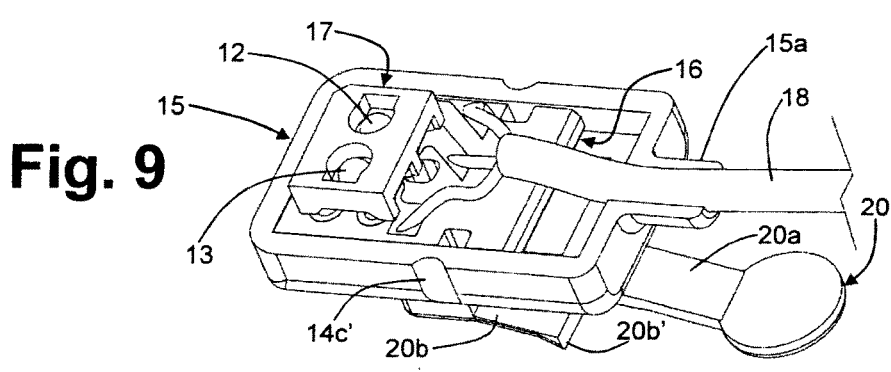

In a preferred embodiment, such as the one exemplified, the emitter and the receiver of electromagnetic radiation, designated by 12 and 13 in FIG. 9, are completely housed within the casing 11 and face a wall of the latter that is at least in part transparent to electromagnetic radiation. This wall of the casing 11, here its lower wall, designated by 11*a*, faces the wall or surface 9*d* of the support 2 and the upper surface of the absorbent layer 4, designated by 4*b*, when the casing 11 is in its predetermined position on the support 2, i.e., in its receiving seat 9.

The material constituting the wall 11*a* is preferably, but not necessarily, identical or similar to a material of the body 3 or of at least its wall 9*d* or its upper part 6. This material may be a polypropylene, or a polyethylene, or a polycarbonate, or a polystyrene. The material of the casing 11 may also be relatively stiffer than the material constituting the body 3 or a part thereof. Indicatively, the thickness of the wall 11a, in its part traversed by the radiation, may be comprised between 0.1 mm and 2 mm, preferably between 0.5 mm and 1 mm.

Preferably, the casing 11 is made up of at least two parts, designated by 14 and 15, here shaped like two generally hollow half-shells that each define the lower wall 11a and the upper wall 11b of the casing, respectively, as well as respective portions of the side and end walls of the casing. The two parts 14 and 15, which can be coupled by snap action, or else welded or glued together, preferably envisage a series of coupling and positioning pins 14a on one part (here the part 14) and corresponding receiving cavities—not shown—on the other part (here the part 15). Advantageously, at least some of the pins 14a function as positioning elements also for a circuit board 16, associated to which are the emitter 12 and the receiver 13, which are preferably integrated in a single opto-electronic body or component of a commercial type, designated by 17.

As already mentioned, in one embodiment, the emitter and the receiver 13 are constituted by an emitter diode, preferably operating in the infrared, and by a phototransistor. The opto-electronic component 17 that integrates the emitter and the receiver is preferentially a commercial component: for example, opto-electronic components that can be used for the purpose are the ones produced by Vishay Intertechnology, Inc. and identified by the codes TCRT500, TCRT100, TCND5000, VCNL4000, CNY70, or produced by Everlight Electronics Co. Ltd, and identified by the code ITR20001/T.

In the example, connected to the circuit board 16, and hence to the emitter 12 and the receiver 13, are the conductors of an electric cable 18 for connection to a monitoring and control unit, which is not represented in so far as it does not form a specific subject of the invention and may possibly be integrated in a medical apparatus, such as an apparatus for haemodialysis. The end of the electric cable 18 opposite to the one connected to the sensor 10 is preferentially provided with a male or female multipolar electrical connector (not represented) for connection to a corresponding female or male connector, respectively, for example provided on the monitoring unit. In general terms, the aforesaid monitoring and control unit is prearranged for analysing—after prior possible treatment (amplification) and/or processing—an electrical signal generated by the receiver 13 and, in the event of a significant variation of the signal with respect to a certain value or a certain range of values, for issuing an alarm, for example of an acoustic and/or light type, and/or controlling safety devices, such as electrical actuators or solenoid valves or electric pumps.

Preferably, the two parts 14 and 15 of the casing 11 each define a part of a respective recess 11c', as well as a respective portion 14b, 15b of a wire-way, preferably shaped for withholding the cable 18 in a stationary position with respect to the circuit board 16. Once again with reference to the example illustrated in FIGS. 6-9, the wall 11a of the casing 11 that the emitter 12 and the receiver 13 face is made at least in part of a material transparent to electromagnetic radiation.

Preferentially, the entire casing 11 of the sensor 10 is made of a material transparent to electromagnetic radiation, even though it is not excluded that it can be made of this material limitedly to a part thereof, such as its part 14 including the lower wall 11a.

Figure 10:
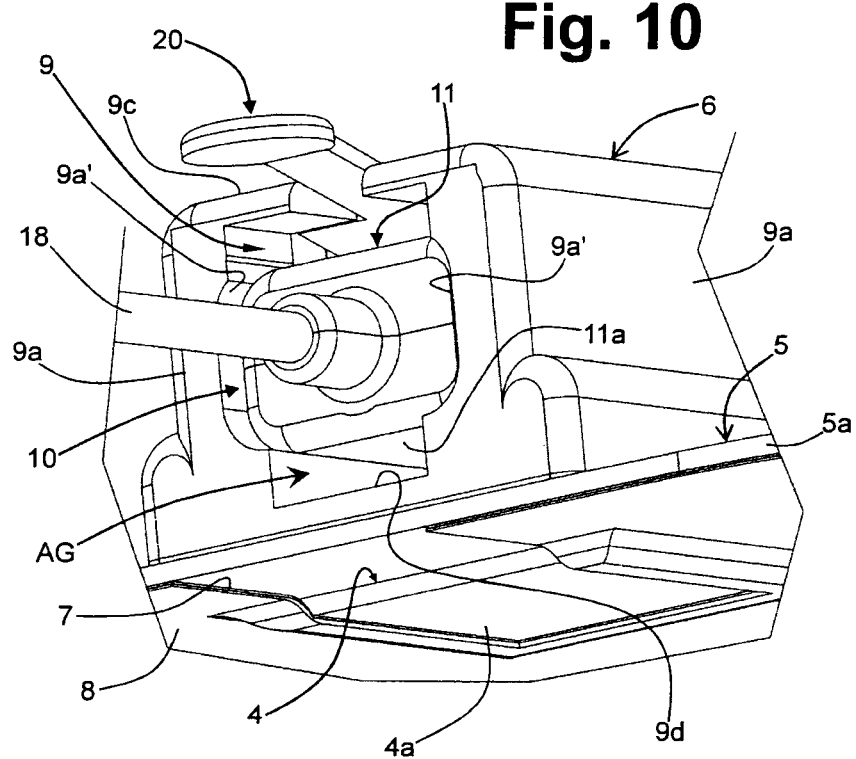
FIG. 10 is a perspective view at an enlarged scale of a detail of a device according to the present invention.
Figure 11:
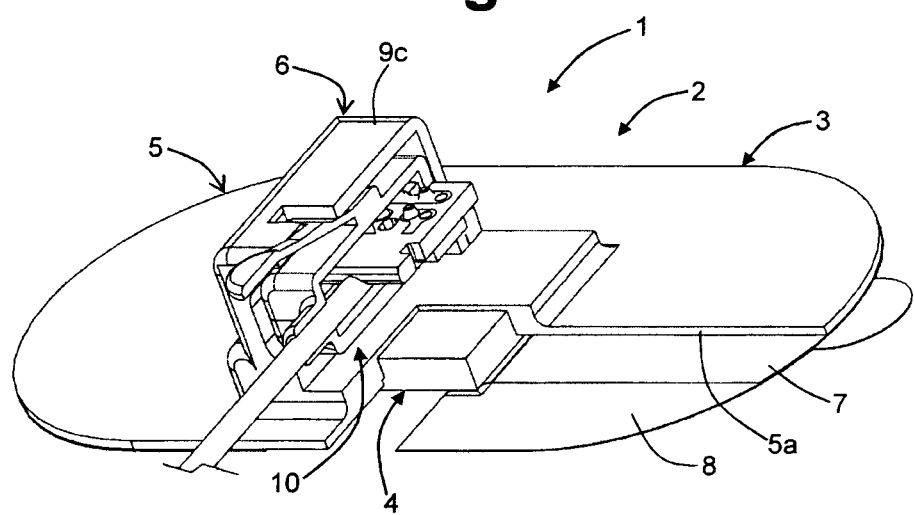
FIGS. 11 and 12 are a partially sectioned perspective view and a corresponding detail, respectively, of a device according to the present invention.

As may be appreciated, for example from FIG. 10, when the casing 11 is in the respective predetermined retention position, here identified by the receiving seat 9, the transparent wall 11a of the casing and the transparent wall 9d of the supporting body 3 face one another. In the specific example illustrated, the aforesaid walls 11a and 9d are set at a distance from one another, i.e., separate from one another by a visibly appreciable air gap, designated by AG. As will emerge clearly hereinafter, the height of the gap AG, when envisaged, is predefined on the basis of the active optical components of the sensor 10, according to the corresponding optimal focal distances. On the other hand, in possible variant embodiments, and according to the type of optical sensor used, the two walls 11a and 9d are substantially in contact with one another.

In FIGS. 10-13, the sensor is in the corresponding predetermined position within the receiving seat defined in the upper part 6 of the body 3, the structure of the device 1 being clearly visible from the sectioned views. In particular, from FIGS. 12 and 13 it may be appreciated how the seat 5b for the absorbent layer 4 is defined between the base 5 and the upper part 6 of the body 3, with the wall 9d of the latter that defines the bottom of the seat 5b. As already explained, following upon application of the strip 7, the layer 4 is blocked in position in the seat 5b, preferably in a condition of at least slight compression of the upper surface thereof 4b against the wall 9d.

Preferably, the surface 4b has characteristics or a configuration such as to improve the characteristics of optical reflection, in particular in the area of interface between the layer 4 and the wall 9d.

In one embodiment, the surface 4b is substantially such as to absorb and distribute effectively the leakage fluid over the bottom wall of the seat 5b, i.e., over the lower surface of the wall 9d, in such a way that the aforesaid fluid alters the optical characteristics thereof from a reflecting condition to a substantially refractive condition.

Figure 12:
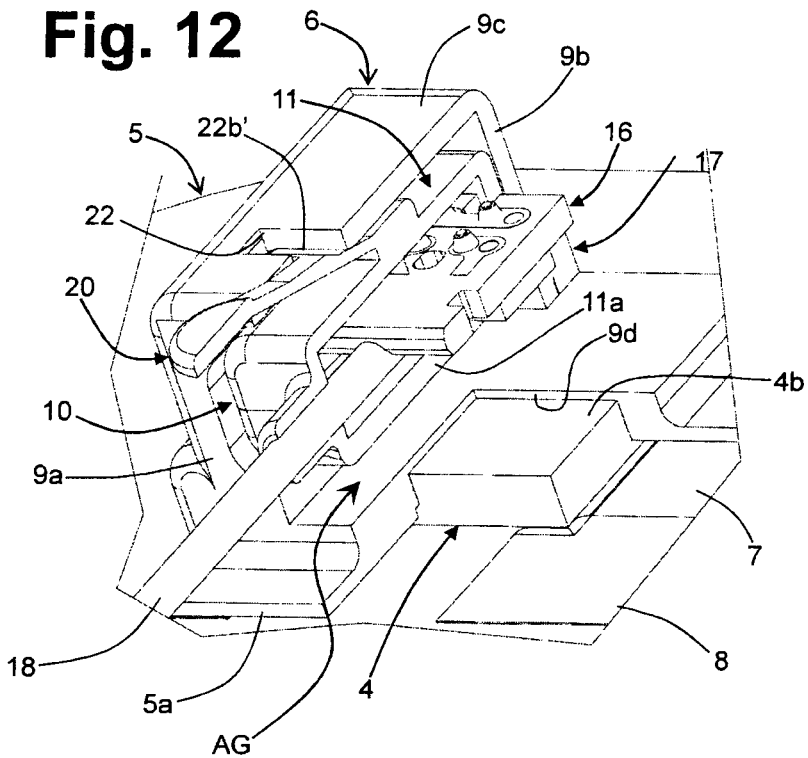
Figure 13:
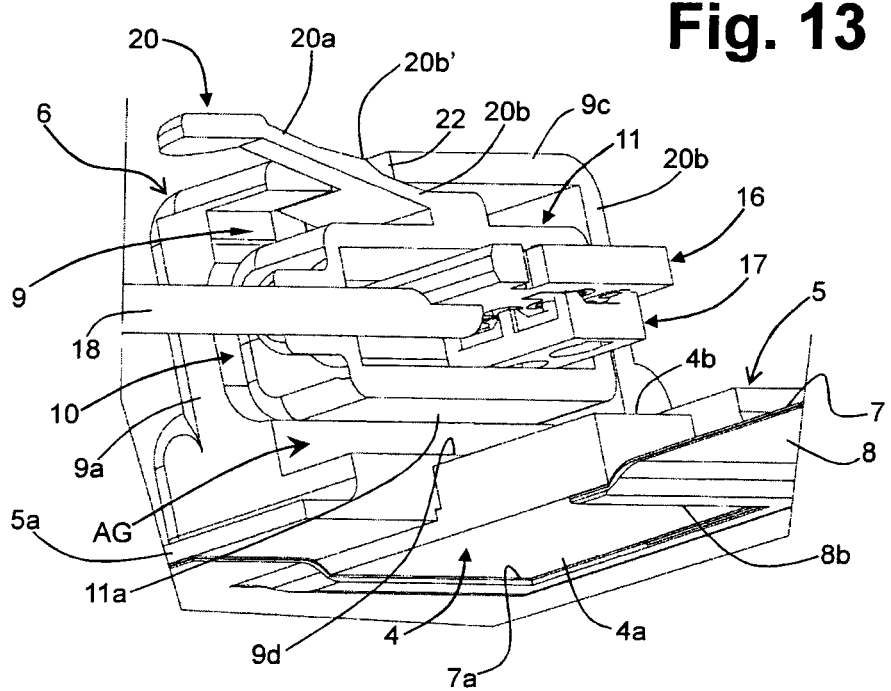
FIG. 13 is a detail of a partially sectioned perspective view similar to that of FIG. 11, from a different angle.

From FIGS. 12 and 13 it may also be noted how, in the condition where the device 1 is assembled, the wall 11a of the casing 11 faces the wall 9d of the body 3, at a distance therefrom, and hence also faces at a distance the upper surface 4b of the layer 4.

The predetermined position of the casing 11, and hence of the emitter 12 and of the receiver 13, is obtained thanks to the presence of the mutual-coupling means previously mentioned. As has already been pointed out, these coupling means are preferentially separable or releasable coupling means in such a way that, if so required, removal of the casing 11 from its predetermined position on the supporting body 3, i.e., from the receiving seat 9, is also enabled. Consequently, as has been said, the sensor 10 can constitute a reusable element, whereas the support 2 is to constitute a disposable or single-use element of the device.

In one embodiment, such as the one exemplified, the coupling means comprise a releasable engagement device, which includes at least one engagement element on the casing 11 and a corresponding retention element on the support 2, and specifically on its body 3: obviously, also possible is a reverse arrangement of the two elements of the engagement device.

Figure 6:
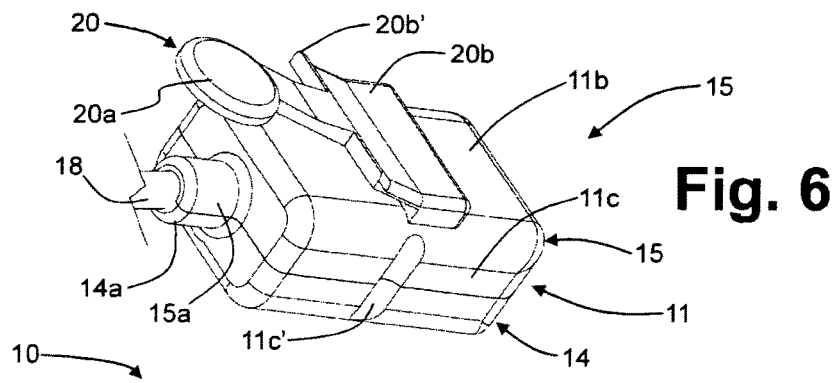
FIGS. 6 and 7 are perspective views, according to different angles, of an optical sensor of a device according to the present invention.
Figure 7:
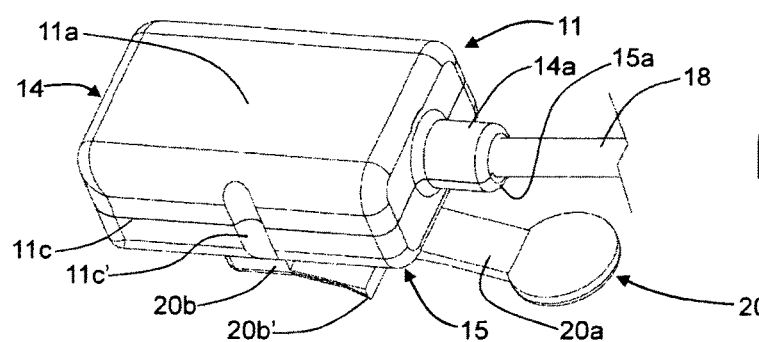
Figure 8:
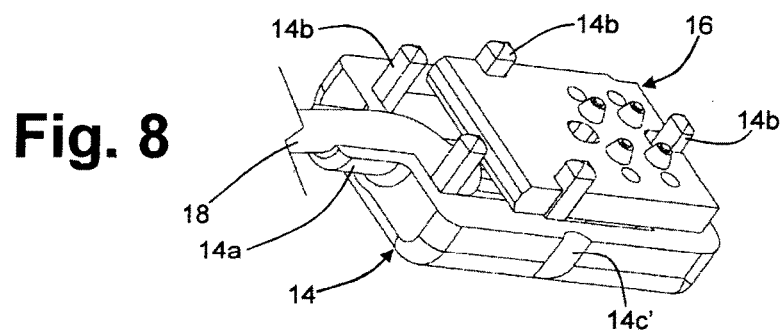
FIGS. 8 and 9 are partial views of the optical sensor of FIGS. 6-7.

With reference to the non-limiting example illustrated in the figures, such an engagement element is designated as a whole by 20 and preferably includes at least one elastically deformable part, associated to or made integrally with a part of the sensor casing 11. With reference to FIGS. 6 and 7, the engagement element 20 is here basically an elastically deformable or flexible tab, which rises from the upper part 15 of the casing 11, with a generally inclined or oblique configuration. The tab 20 basically comprises a proximal portion 20a for gripping or manual actuation and a distal, engagement, portion 20b, with the latter that is able to co-operate with a respective retention formation defined in the supporting body 3. In the example, the proximal portion 20a has a smaller width than the distal portion 20b so that the front edge 20b' of the latter—possibly tooth-like shaped—forms an engagement element. On the other side, the aforesaid retention formation is here defined in a position corresponding to the upper wall 9c of the receiving seat 9. As may be noted, for example in FIG. 5, defined in the aforesaid upper wall 9c, starting from its front edge, is an axial cut 21 which follows, once again in the wall 9c, a transverse cut 22, substantially orthogonal to the cut 21 and preferably—but not necessarily—communicating therewith. The transverse cut 22 preferentially has a length only slightly greater than the width of the edge 20b' of the engagement portion 20b of the tab 20: in this way, when the casing 11 is inserted from the front within the seat 9, between the upper end of the portion 20b of the tab 20 and the upper wall 9b of the seat there is created an interference, with a consequent bending of the tab as insertion proceeds. The cut 21 and/or the cut 22 could be replaced by technically equivalent elements, such as a seat in the form of a blind cavity on the inside of the wall 9c, provided that their function described hereinafter is preserved.

The restricted gripping portion 20a penetrates into the longitudinal cut 21, with the casing 11 that can be pushed into the seat 9 until the edge 20b' of the engagement portion 20b of the tab 20 reaches the transverse cut 22 and the elastic reaction of the tab determines engagement of the edge with the transverse cut. When such an engagement is obtained, the casing 11 is set in a substantially predefined and fixed position within the receiving seat 9. It appears equally evident that, via a simple pressure downwards of the gripping portion 20a of the tab 20, disengagement of the aforesaid edge 20b' from the cut 22 can be obtained, thereby enabling subsequent extraction of the casing 11 from the seat 9. It will be appreciated that an end of the proximal portion 20a of the tab 20 projects constantly on the outside of the seat 9, and as such represents an element that can be gripped, which facilitates removal of the casing 11 from its position defined by the seat 9, enabling manual pulling thereof.

In one embodiment, the mutual-coupling means between the sensor casing 11 and the supporting body 3 comprise sliding and/or positioning guides, which include at least one guide element on the support and at least one corresponding guided element on the sensor casing. For instance, with reference once again to the embodiment illustrated, and as may be seen in FIGS. 4 and 10, two opposite walls of the casing 11, represented by the side walls designated by 11c in FIGS. 6 and 7, have an outer surface profile that is substantially complementary to at least one portion of the inner surface profile of two corresponding side walls of the seat 9, here represented by the side walls 9a.

Preferentially, as in the example described, coupling between the side walls 11c of the casing 11 and the side walls 9a of the seat 9 is substantially a shape fit, which enables the casing to be guided in an extremely precise way as far as its predetermined retention position. In the example, the inner-surface profile of the walls 9a includes a respective longitudinal recess or slot, designated by 9a' in FIG. 5, such as a seat with partly rounded profile, which is substantially complementary to a profile of the side walls 11c of the casing 11 and includes rounded areas.

Once again from FIG. 5 it may be noted how the recesses 9a' are located in an intermediate area in height of the inner surfaces of the walls 9a, so that—in the assembled condition, as for example may be seen in FIG. 10—between the upper wall and the lower wall of the casing 11 and the corresponding upper wall and lower wall of the seat 9 there are in any case defined an upper gap and a lower gap, the first enabling housing of part of the tab 20 and the second determining an air gap between the walls 11a and 9d that are transparent to electromagnetic radiation.

As will emerge clearly hereinafter, the guide means can be differently shaped and/or comprise elements that fulfil also further functions, such as a function of key for insertion of the sensor casing in the corresponding predetermined position.

In one embodiment, the mutual-coupling means include at least one surface relief of one between the sensor casing and the supporting body and at least one corresponding recess of the other between the sensor casing and the supporting body, where the relief and recess are mutually engageable and releasable following upon positioning and removal, respectively, of the sensor casing with respect to the predetermined position or with respect to the inside of the corresponding receiving seat.

With reference once again to the example illustrated, on the opposite side walls of the sensor casing—here the side walls 11c of FIGS. 6-7—respective slots are provided, here generally elongated or vertical slots designated by 11c', preferably with semicircular cross section, which are to co-operate with reliefs of a complementary shape provided on opposite walls of the seat 9—here the side walls 9a of FIG. 5. One of these reliefs, here configured as a generally elongated or vertical relief, preferably with semicircular cross section, may for example be seen in FIGS. 4 and 5, where it is designated by 9a". Obviously, a reverse arrangement is possible, with recesses in the walls 9a of the seat 9 and reliefs in the side walls 11c of the casing 11, and/or different shapes, provided that they can be coupled together. As may be appreciated, the slots 11c' and reliefs 9a" basically operate as a snap-action engagement device and/or as a snap-action positioning means, which can be provided as an alternative to or in combination with the elastic engagement device described previously with reference to the tab 20.

In such an embodiment, it is preferable for at least one of the two parts involved, i.e., the part that defines the walls 9a of the seat 3, on one side, and the sensor body 11, on the other, to be made of a material at least slightly elastically yieldable or deformable, for example a soft PVC or a TPE or a TPU, for enabling coupling and possible uncoupling of each relief 11c' with respect to the corresponding recess 9a" during insertion, respectively extraction, of the casing 11 with respect to the seat 9. On the other hand, in embodiments here not represented, in which the seat that defines the predetermined position for the optical sensor comprises just two opposite side walls that rise from the base 5, it is also possible to make these walls of a relatively rigid material, provided that they can in any case divaricate at least slightly in an elastic way in order to enable engagement/disengagement between the slots and reliefs.

The slots 11c' and reliefs 9a" preferably provide snap-action positioning means designed to define or improve precise positioning of the optical sensor 10 and/or the corresponding casing 11 with respect to the support 2, 3 and/or to the corresponding seat 9.

Preferentially, in the case of coexistence of the two engagement systems 20-22 and 9a"-11c', these will be configured in such a way that the respective passages from the engagement and released conditions—induced by insertion, respectively extraction, of the casing 11 into/from the seat 9—occur simultaneously.

As has been mentioned, in one embodiment the positioning and/or mutual-coupling means comprise a key or combination, for unique or exclusive positioning of the casing 11 in its predetermined position on the body 3, or in the seat 9, or more in general a unique coupling of the sensor 10 with a respective support 2.

Such a key includes at least one first key element on the sensor 10, here on its casing 11, and at least one second key element on the support 2 or its body 3, with the second key element that is able to co-operate uniquely with the first key element. With reference once again to the non-limiting example so far illustrated, this key or combination may be obtained by combining the coupleable complementary profiles of the walls 9a of the seat 9 and of the walls 11c of the casing 11 with the releasable engagement device described above, including the cut 21 in which the portion 20a of the tab 20 can be inserted. It is evident that, given the presence of these elements, the casing 11 can only be inserted with a unique orientation in its predetermined position, without any possibility of error. According to other embodiments (not represented) other seats and/or reliefs can be provided on the sensor 10 and on the support 2, that can be coupled together uniquely or in a complementary way to define a coupling and/or positioning key.

As already mentioned, in a preferred embodiment of the invention, the supporting body 3 integrates in a single piece the upper part 6, which here defines the positioning seat 9, and at least a substantial portion 5a of the resting base 5, there being associated to the latter the absorbent layer 4, preferably kept in position via at least one strip 7, or other adhesive or welding or engagement means. Obviously, the conformation of the body 3 and of the layer 4 and the corresponding modalities of mutual fixing are provided merely by way of example and may undergo variations. For instance, the strip 7 could be set between the laminar portion 5a of the base 5 and the absorbent layer 4, with the latter that in any case can penetrate at least in part into the corresponding lower cavity 5b, possibly as far as the condition of at least slight compression of the upper surface 4b against the wall 9d.

Figure 14:
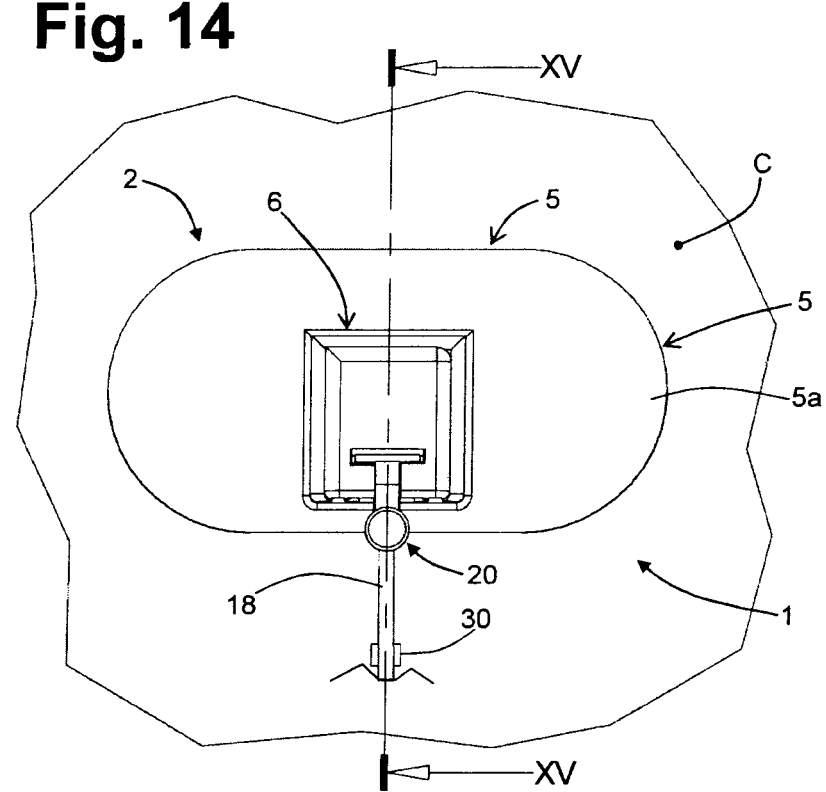
FIG. 14 is a schematic representation in top plan view of a medical detection device according to the invention in an example of operating condition.
Figure 15:
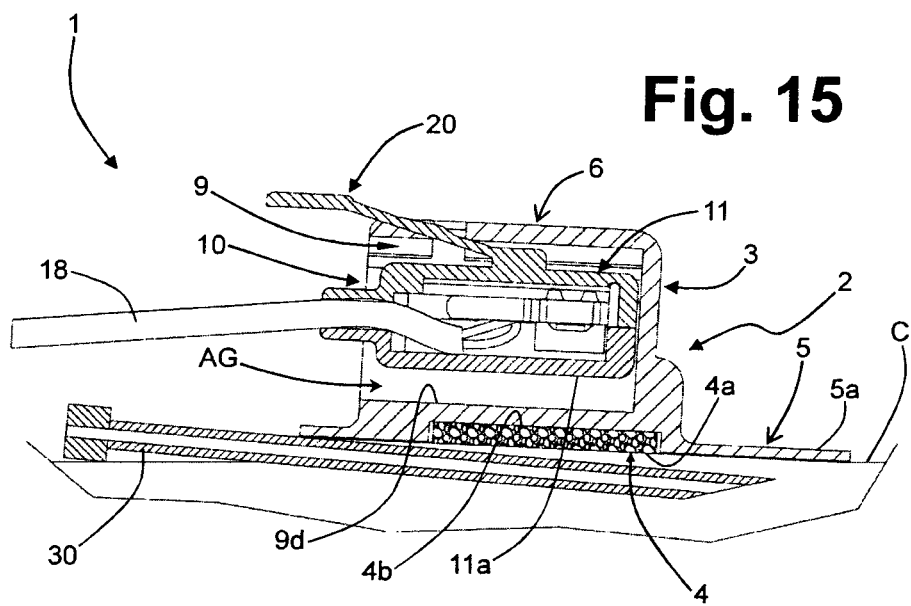
FIG. 15 is a schematic cross-sectional view according to the line XV-XV of FIG. 14.

FIGS. 14 and 15 represent schematically an example of application of the detection device 1 to the skin or body of a patient, designated by C. The device 1 is positioned on the skin C of the subject in the proximity of the wound made by insertion of a needle or a cannula 30 in a vein or artery, as may be seen in FIG. 15. From the cross section of FIG. 15 it may be noted how the layer of absorbent material 4 is preferably in contact with the skin C, in particular in the proximity of the wound formed by insertion of the cannula. The support 2 can be fastened to the skin C, exploiting the adhesiveness of the lower face of the strip designated previously by 7, after the protective strip designated previously by 8 has been removed; on the other hand, in addition or as an alternative, it is also possible to fasten the support 2 to the skin C using additional means, such as plasters, medical adhesive tapes, bandages, etc.

For instance, in the case of a leakage from the wound made by insertion of the needle or cannula 30, the blood reaches the lower surface of the layer 4, and then spreads within it, until it causes a variation of one or more optical properties at its upper surface 4b and/or at the surface 9d of the support 2 (in particular, the surface that forms the bottom of the seat 5b), for example a variation of the characteristics of reflection of incident radiation, or once again a variation of colour.

The above variation can be detected via the optical sensor 10, as described hereinafter, so that the corresponding monitoring unit can issue an alarm and/or control other devices. It should be noted that the lower surface of the layer 4 could be also slightly raised with respect to the skin C, but a leakage of blood that spreads in the vicinity of the wound resulting from insertion of the needle or cannula comes in any case into contact with the layer 4, impregnating it as far as the upper surface thereof. It should be noted in this regard that the thickness of the layer 4 is relatively contained and that the material used is highly hydrophilic, so that the rate of impregnation of the layer is very high.

Figure 16:
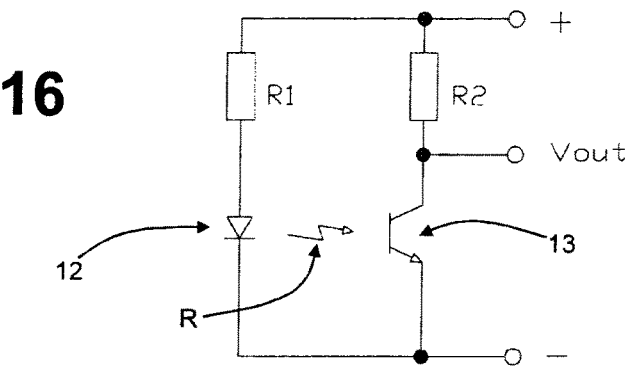
FIG. 16 is a simplified circuit diagram of an optical sensor that can be used in a medical detection device according to the invention.

FIG. 16 represents, merely by way of example, a possible circuit configuration of a sensor that can be used in a device according to the invention, in which the emitter 12 and the receiver 13 are constituted by a photodiode and a phototransistor, respectively, which are designed to generate and receive, respectively, a beam of electromagnetic radiation R. In this configuration, the emitter 12 and the receiver 13 are connected to a positive supply line "+", in particular by means of respective resistors R1 and R2, and to a negative supply line "−". Furthermore, the receiver 13, in particular the collector of the phototransistor that constitutes it, is connected to a terminal Vout. The difference of potential between the terminal Vout and the negative supply line "−" indicates radiation of light received by the receiver 13: it will be appreciated that in this way the terminal Vout can be used for detecting an electrical signal corresponding to the beam R emitted by the transmitter 12, when this beam is received by the receiver 13.

Figure 17:
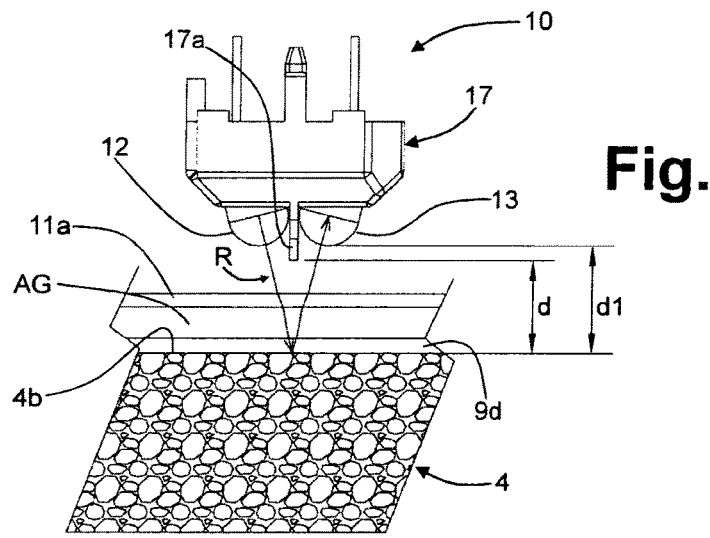
FIGS. 17 and 18 are schematic representations aimed at exemplifying the operating principle of an optical sensor of a device according to the invention.
Figure 18:
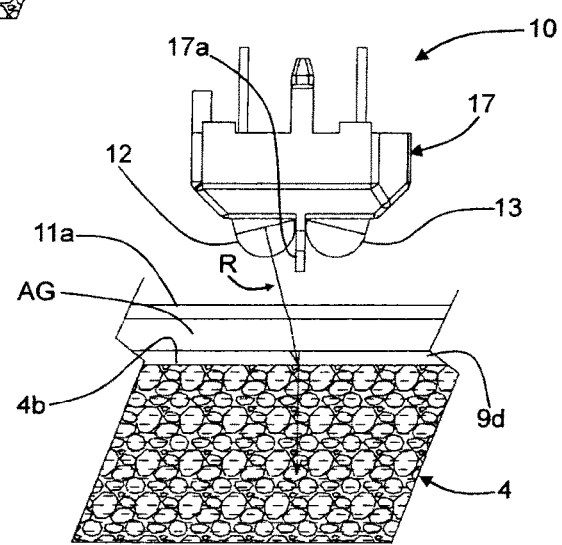
Figure 22:
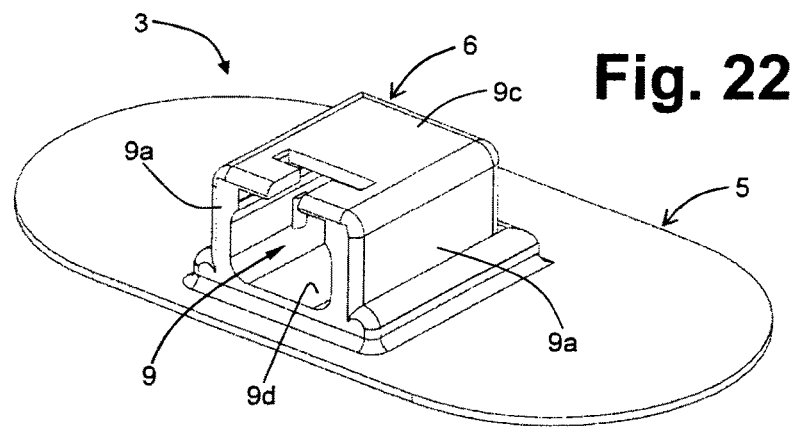
FIG. 22 is a perspective view of a supporting body of the device of FIG. 20.
Figure 23:
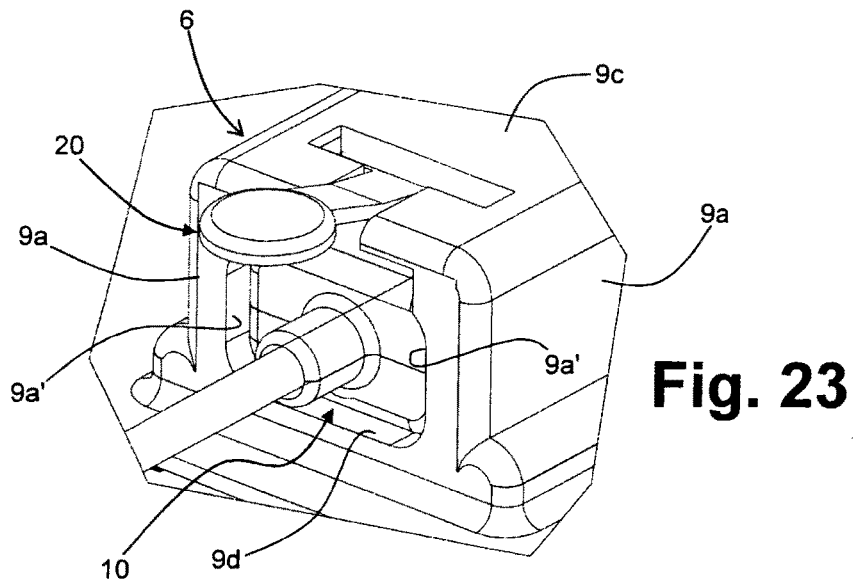
FIG. 23 is a detail at an enlarged scale of the device of FIG. 21.
Figure 24:
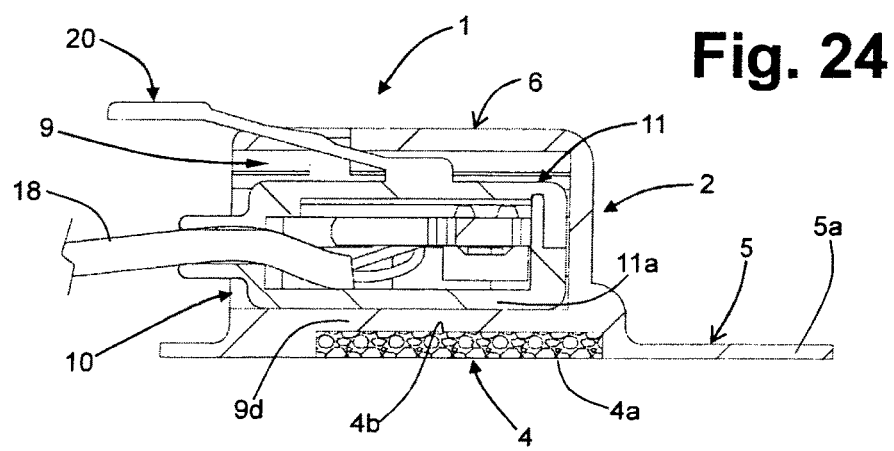
FIG. 24 is a schematic cross-sectional view of a body of the device of FIG. 21 with a corresponding optical sensor associated thereto.

FIGS. 17 and 18 illustrate the general operating principle of an optical sensor according to an embodiment in which the support of the device presents an absorbent layer 4.

Very schematically, via the emitter 12 the electromagnetic radiation is emitted with a predefined wavelength or a wavelength comprised in a predefined range of wavelengths, for example radiation in the infrared, the beam R of which reaches the interface between the lower surface of the wall 9d and the upper surface 4b of the absorbent layer 4. In its path, the beam R is transmitted through the wall 11a of the sensor casing, the air gap AG and the wall 9d of the body 3, as far as the lower surface of the wall 9d and/or the upper surface 4b of the layer 4. As mentioned previously, the walls 11a and 9d are made of a material transparent to the radiation of the beam R. In the passage between the transparent walls and the air gap the beam R is subject to slight angular deviations, which according to the example have, however, a negligible effect for the purposes of operation of the optical system.

FIG. 17 exemplifies the neutral or anhydrous condition of the layer 4 (i.e., where it is not soaked with liquid). Very schematically, at the interface between the upper surface 4b of the layer 4 and the lower surface of the wall 9d the beam R, or at least a substantial part thereof, is reflected towards the receiver 13 (effects of refraction or diffusion are negligible). For this purpose, preferably, the optical axes of the emitter 12 and of the receiver 13 are adequately inclined with respect to the normal of the aforesaid interface, in particular in order to direct the higher intensity of the beam R in the focal point or predefined point of reflection. Also the distance between the emitter and the receiver, on one side, and the surface 9d and/or the surface 4b, on the other side, are pre-set and ensured thanks to the positioning means described above. The reflected beam R is detected by the receiver 13, to give rise to an electrical signal, such as a voltage Vout, which, in the anhydrous condition of the layer 4 and/or of the wall 9, has a certain first value or is comprised in a given predefined range of values.

FIG. 18 exemplifies, instead, a condition where the layer 4 is soaked with liquid, which in the specific example is assumed as being leaked blood. Following upon its diffusion through the layer 4 (for example, owing to phenomena of capillarity), the blood reaches the upper surface 4b thereof, coming into contact with the lower surface of the wall 9d, thereby causing a variation of one or more optical characteristics of these surfaces, i.e., of the corresponding interface, specifically of the corresponding properties of reflection and/or refraction, such that a substantial part of the beam R is no longer reflected at the receiver 13. In the schematic example represented, the aforesaid substantial part of the beam R is transmitted in the system constituted by the absorbent layer and the blood (a part of the beam F may also be reflected, but with negligible effects).

Corresponding to the reduction of electromagnetic radiation detected by the receiver 13 is a variation of the electrical signal generated by the receiver itself, i.e., a second value of the voltage Vout, such as a significant reduction with respect to the aforesaid first value of the signal or with respect to the lower threshold value of the range of values mentioned previously.

The variation of electrical signal is detected via the control electronics of the monitoring unit to which the sensor 10 is connected. The control logic of the aforesaid unit interprets the variation detected as indicating a leakage of fluid or blood and consequently governs activation of the alarm and/or of other devices (for example, solenoid valves and/or electric pumps and/or electric motors and/or electric actuators, etc.).

In FIGS. 17 and 18, the heights designated by d and d1 refer to the focal distance or distance of optimal reflection with respect to a reference element 17a of the component 17 and with respect to its active optical elements (i.e., the lenses of the transmitter 12 and of the receiver 13); in particular, these heights d and d1 are comprised between 0.2 mm and 20 mm, preferably between 1 mm and 6 mm.

In the case of use of a device 17 with relatively large heights d and d1 (for example, d comprised between 5 and 6 mm) a configuration of the device 1 distinguished by the presence of the air gap AG is preferable, whereas for relatively low heights d and d1 (for example, d comprised between 1 and 2 mm) it is preferable to adopt a configuration of the device with the walls 11a and 9d substantially in contact, as exemplified hereinafter with reference to FIGS. 21-24. For intermediate heights of d and d1 (for example d comprised between 3 and 4 mm) it is possible to adopt both configurations of the device 1 with the air gap AG, if very thin walls 11a and 9d are adopted (for example, two walls of 0.5 mm and an air gap of 2 or 3 mm), and configurations with relatively thick walls 11a and 9d (for example, two walls of 1.5 or 2 mm each) in contact with one another.

In general terms, then, various configurations of walls or layers of material transparent to radiation may be envisaged, which separate the active components 12-13 of the optical sensor 10 from the absorbent layer 4 and/or from the fluid to be detected, such as for example:

two transparent walls or layers and two air gaps, as in the case exemplified in FIGS. 1-19 (where one air gap is the one set between the walls 11a and 9d and the other air gap is the one existing between the wall 11a and the optical elements of the emitter 12 and of the receiver 13);

a transparent wall or layer and an air gap (as has been mentioned, the optical receiver and emitter elements could project from the casing 11 or face towards the outside thereof);

two transparent walls or layers and an air gap (where the air gap is the one set between the walls 11a and 9d, and the optical elements of the emitter 12 and of the receiver 13 are in contact with the wall 11a);

two transparent walls or layers in contact with one another, as exemplified in FIGS. 20-23, with or without an air gap between the optical elements of the emitter 12 and of the receiver 13 and the wall 11a.

FIGS. 19 and 20 regard further possible configurations of the principle diagram of FIGS. 17 and 18, i.e., variants of the device 1, aimed at optimizing the optical operation of the sensor 10 by adopting lenses. For instance, in the case of FIG. 19, the wall 11a of the sensor casing is shaped so as to define at least one lens 11a', such as a first lens or portion of lens on a first surface of the wall 11a and a second lens or portion of lens on the opposite surface of the wall 11a, whereas in the case of FIG. 20 both the wall 11a of the casing and the wall 9d of the supporting body are shaped so as to integrate respective lenses, designated by 11a' and 9d'.

Adoption of one or more lenses enables modification of the focal distance of the optical sensor 10 in order to optimize the device 1 with respect to the various types of transmitters and receivers used, or to the opto-electronic components that integrate them. For instance, the cases represented schematically in FIGS. 19-20 regard use of an opto-electronic component 17', the emitter 12 and receiver 13 of which are more distant from one another and/or differently angled with respect to the case of the component 17 of FIGS. 16-17, with corresponding focal or reflection point that are very distant.

With the simple adoption of this component 17' on the structure of FIGS. 16-17 there would be a focal distance between the layer 4 or the lower surface of the wall 9d, on one side, and the emitter and the receiver, on the other, which would not enable correct operation of the detection system; i.e., it would be necessary to set said lower surface of the wall 9d at a considerable distance from the sensor 10. Adoption of one or more lenses thus enables optimization of the focal distance according to the type of opto-electronic component used, reducing, if so required, the aforesaid focal distance and hence the overall dimensions of the device 1.

In a preferred embodiment, the wall 9d and/or the wall 11a have/has at least one surface with a substantially given roughness.

Preferentially, the transparent wall 11a of the sensor body 11 has—at least in the area thereof corresponding to the wall 9d—a substantially given roughness, in particular in a position corresponding to its two opposite surfaces, which are not necessarily the same as one another. Once again preferentially, the wall 9d of the support 2 has, at least in its area corresponding to the layer 4, a surface with a first substantially pre-determined roughness, such as a substantially smooth surface, and more in particular the surface of the wall 9d facing the sensor 10 has a second roughness, preferably a second roughness greater than the first roughness; i.e., it has a rough surface towards the sensor 10 and a smooth surface towards the layer 4.

The surfaces with a second substantially pre-determined roughness, and in particular the surfaces with a similar second roughness of the wall 11a, basically have the function of preventing or reducing undesirable reflections in areas different from the ones of the interface between the lower surface of the wall 9d and the upper surface of the layer 4, these undesirable reflections otherwise possibly causing an anomalous excitation of the sensor 10, or in any case varying the level of its output signal Vout.

Consider that the optical beam designated previously by R in the figures is that of greater intensity. However, in actual fact, the emitter 12 irradiates also additional differently angled light beams, the intensity of which decreases as the corresponding angle increases: these further light beams could even so manage to excite the sensor 10 by reflecting in some other point.

It should be pointed out that the device 1 is able to function in any case also with walls having completely smooth surfaces, but the configuration with at least some rough surfaces makes it possible to obtain signals at output from the sensor with clearer variations, i.e., ones that can be discriminated more easily, in particular by the electronic control circuit. The presence of rough surfaces thus enables reduction of the risk of the sensor generating an anomalous output signal.

The fact that one or more surfaces of the walls 9d and 11a may even be rough moreover enables simplification of the moulding equipment. Consider that, even given one and the same transparent material, the quality of the surface finish of the support 2 and/or of the casing 11 depends upon the characteristics of the moulding equipment, i.e., upon the surface finish of the corresponding mould, upon which the surface finish or roughness of the corresponding surfaces of the moulded components depends. To obtain a very smooth surface, this must be obtained with a mould having a wall polished in an area where this surface is to be formed. According to the preferred solution outlined above, the mould can be prepared with a polishing limited to a part thereof that is to form a detection surface, i.e., the lower surface of the wall 9d, which is to come into contact with the layer 4, enabling instead a poorer surface finish in other parts that are to be moulded, for which it could even be counterproductive to have a practically smooth surface. To obtain a substantially pre-determined surface roughness it is possible, for example, to sand the corresponding portion of mould with abrasive powder of a predefined grain size.

Indicatively, one or both of the rough surfaces of the wall 11a and the upper rough surface of the wall 9d can have values of roughness, expressed in Ra (average roughness) comprised between 0.5 and 30 micrometers; preferably, at least one of the surfaces of the walls 11a and 9d has a roughness comprised between 0.5 and 2 micrometers.

Preferentially, the roughness Ra of one or both of the surfaces of the wall 11a is less than the roughness Ra of the upper surface of the wall 9d; for example, at least one of the surfaces of the wall 11a has a roughness Ra comprised between 0.5 and 2 μm, and at least one of the surfaces of the wall 9d has a roughness Ra higher than 15 μm.

FIGS. 21-24 illustrate a possible variant embodiment of the invention. The embodiment of the device 1 of FIGS. 21-24 to a large extent corresponds to that of the devices described with reference to FIGS. 1-20, with the only substantial difference represented by the fact that, in this case, in the predetermined position of the sensor casing 11, i.e., within the seat 9, the lower surface of its lower wall 11a is substantially in the proximity of or in contact with the upper surface of the wall 9d of the supporting body 3, i.e., in a condition of a reduced air gap AG of FIGS. 17-18 or absence thereof (an extremely small space could, for example, exist on account of typical tolerances or deformations of the moulded plastic materials).

In the example represented, and without prejudice to the other characteristics described, this effect is obtained simply by a different positioning in height of the recesses 9a' of the inner profile of the side walls 9a of the seat 9. In particular, in the example, the recesses 9a' are further down, with the respective lower parts substantially coinciding with the upper surface of the wall 9d of the body 3. In such a case, the height of the walls 9a can be consequently less than in the case of FIGS. 1-20. In the configuration of FIGS. 21-24, there is of course provided an optical sensor with emitter 12 and receiver 13 appropriately set at a distance from one another and/or angled with respect to the case of FIGS. 17-18, in order to obtain the appropriate focal point: as has been said, the configuration of FIGS. 21-24 may be convenient precisely in the case of optical sensors that have a shorter focal distance. For the rest, operation of the device 1 is similar to what has already been described above.

Figure 25:
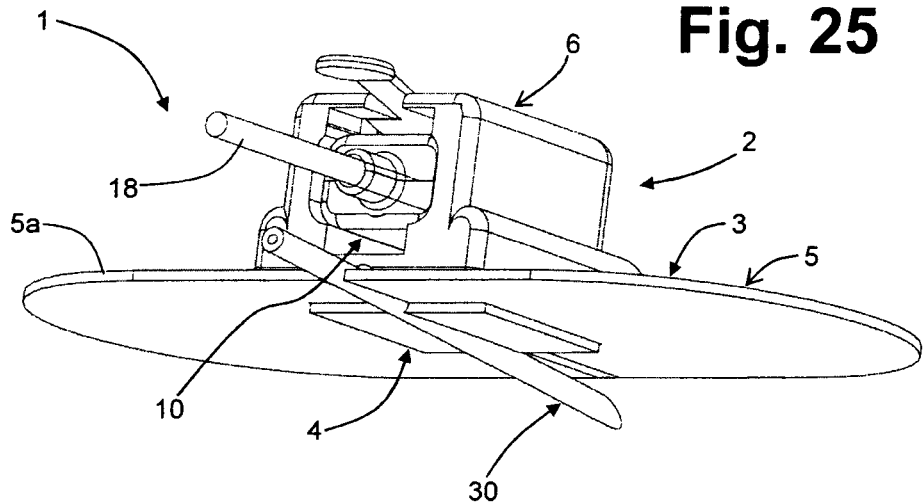
FIG. 25 is a perspective view of a further variant embodiment of a detection device according to the invention.
Figure 26:
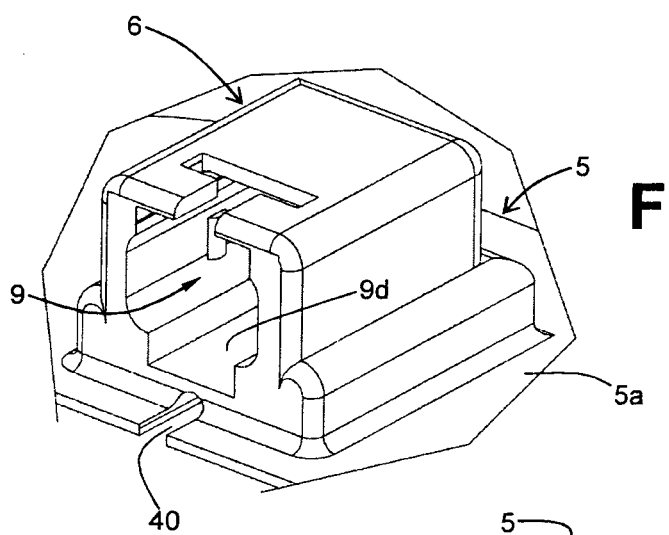
FIGS. 26 and 27 are perspective views of portions of the device of FIG. 25, from a different angle.
Figure 27:
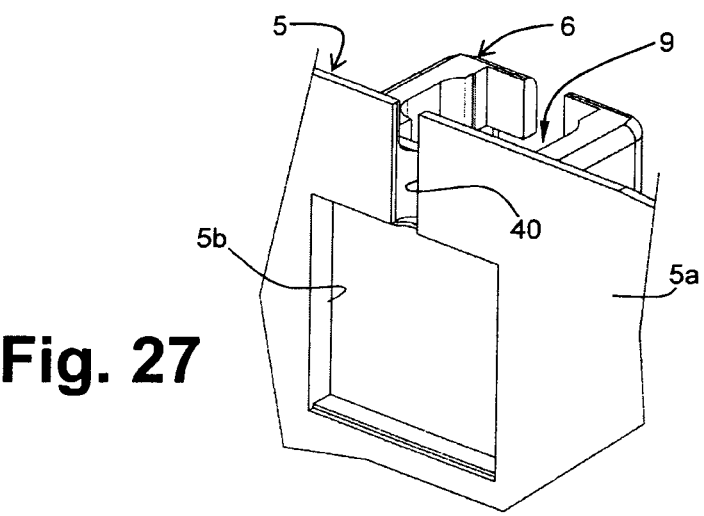

FIGS. 25-27 refer to a further variant embodiment of the invention, basically aimed at enabling an optimization of the corresponding positioning between a device 1 and at least one from between a cannula (or needle) and a corresponding wound due to insertion thereof, for example to be able to position the device 1 with the respective layer of absorbent material 4 in a position very close to the wound caused by insertion of the cannula into the skin of the patient and/or to position it in a more convenient way.

In this embodiment, in at least one between the resting base 5 and the upper part 6 of the supporting body 3 a seat or groove 40 is defined for positioning or housing a respective portion of the cannula 30. In the example represented, the groove 40 extends in the base 5 and, to a minimal extent, also in the upper part 6, between the front edge of the aforesaid base 5 as far as the seat 5b that is to house the absorbent layer 4; the groove 40 is preferably inclined with respect to the axis of the support 2. Possibly, also the layer 4 can be prearranged so as to have a seat or groove, similar or complementary to the seat or groove 40, possibly inclined in order to favour positioning of the cannula. Provision of a seat or groove 40 on the body 3 and/or in the layer 4 may be extremely useful in view of one or more of the following purposes:

enabling coupling of the body 3 to the portion of the cannula 30 that projects from the skin of the patient in order to facilitate centring and/or positioning of the device 1 on the cannula itself;

enabling the device 1 to be on top of the cannula 30 better, without compression of the cannula, preventing anomalous movements thereof and/or pain to the patient;

enabling positioning of the lower surface of the absorbent layer 4 directly in a point corresponding to the wound due to insertion of the cannula 30 in the skin of the patient.

FIGS. 28-32 illustrate with different views a further embodiment of the invention. In these figures the same reference numbers are used as in the previous figures to designate elements that are technically equivalent to the ones already described above. The embodiment of FIGS. 28-32 differs basically from the ones so far described in that the seat 9 for receiving the sensor casing 11 is open at the top; i.e., it has an upper insertion opening or mouth in a position corresponding to the top of the part 6 (i.e., an upper mouth set substantially orthogonal to the front mouth described in the previous examples or with respect to the plane of fixing identified by the base 5).

As may be appreciated clearly, for example from FIG. 30, in this case the upper part 6 of the supporting body 3 rises from the resting base 5 defining four vertical walls, substantially orthogonal and contiguous to one another, and specifically two side walls 9a, a rear wall 9b, and a front wall 9. There is then, of course, provided the lower wall 9d transparent to electromagnetic radiation, in an opposite position to the aforesaid upper mouth.

In the example represented, the mutual-coupling means between the casing 11 and the support 2 comprise a releasable engagement device that includes two tabs 20, which are substantially of the type described previously, but are here associated to the two opposite side walls 11c of the casing 11 and project upwards in a configuration less inclined with respect to the case of FIGS. 1-15, the two tabs 20 being preferably specular to one another. The presence of at least two tabs 20 and/or the corresponding opposed arrangement moreover enables production convenient gripping means to be provided for coupling and/or uncoupling the sensor 10 to/from the support 2. Corresponding longitudinal cuts or seats 21 and transverse cuts or seats 22 are here made on the side walls 9a of the part 6, which correspond to the side walls 11c of the casing 11. As may be appreciated, the operating principle of each of the two tabs 20 of the releasable engagement device of this embodiment is practically similar to what has been described previously. In this embodiment, the electric cable 18 preferably comes out of the upper wall 11b of the casing 11, which is preferably provided with or integrates cable-stop and/or cable-gripping means, not represented in the figures.

Figure 31:
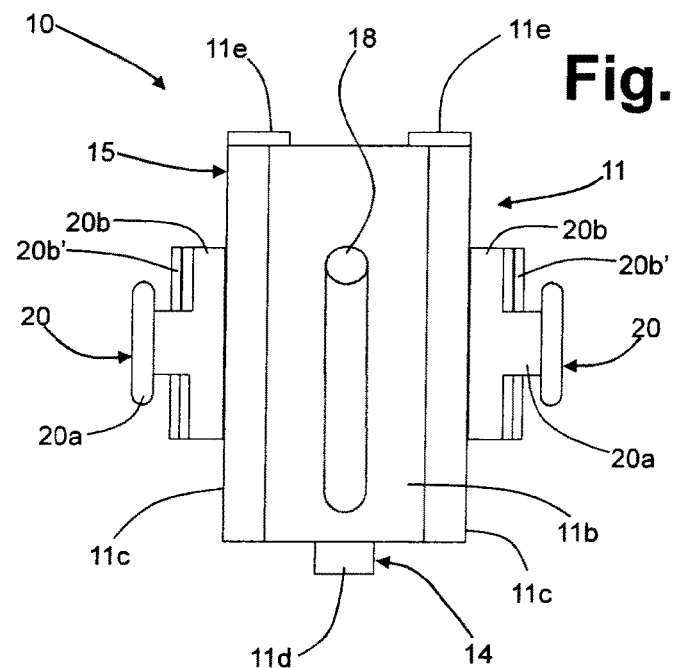
FIG. 31 is a schematic top plan view of the optical sensor of the device of FIGS. 29 and 30.
Figure 32:
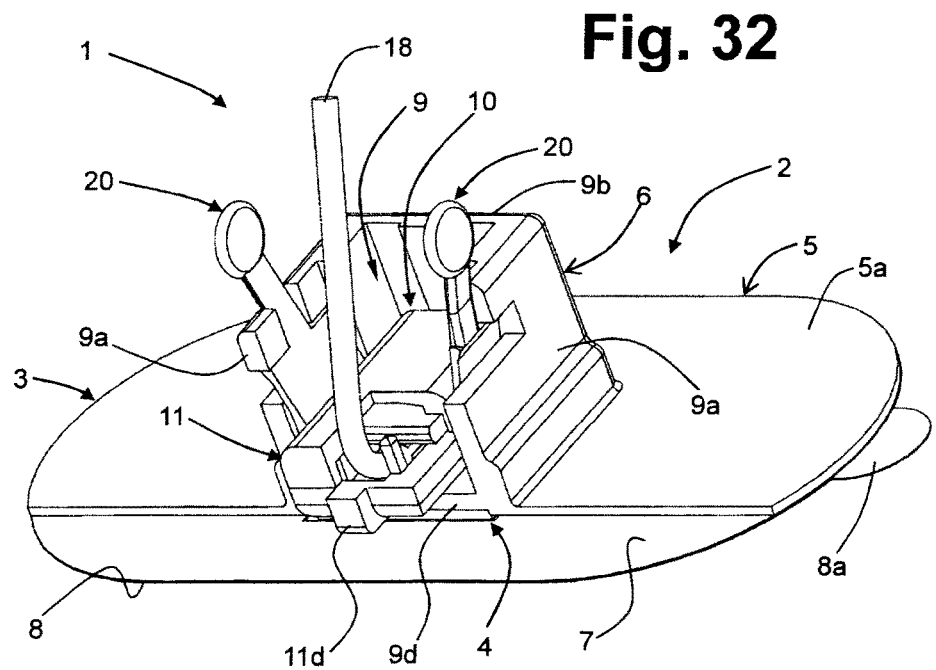
FIG. 32 is a partially sectioned perspective view of the device of FIG. 27.

Also provided in the embodiment of FIGS. 28-32 are guides for insertion of the casing 11 in the seat 9. For instance, with reference to FIGS. 29 and 30, the inner-surface profile of the walls 9a includes vertical recesses 9a', in which the engagement portion 20b of the tabs can be engaged and slide precisely (the width of the portions 20b is slightly smaller than the width of the recesses 9a'), thereby providing guide elements and guided elements, respectively. On the other hand, guides may be provided also on the other walls of the casing 11 and of the seat 9. For instance, in the case illustrated, defined on the inner side of the wall 9e of the seat 9 is an axial recess or slot 9e', whereas defined on the opposite wall 9b is an axial relief or projection 9b'. On the other hand, as may be clearly seen in FIGS. 29 and 30, in a position corresponding to the front wall of the casing 11 an appendage or projection 11d is provided, preferably having a profile substantially complementary to that of the recess 9e' of the front wall 9e of the seat 9, and in any case designed for precise engagement and sliding therein. Instead, as may be seen in FIGS. 30 and 31, provided in the rear wall of the casing 11 are two projections 11e, between which the axial projection 9b' of the rear wall 9b of the seat 9 can be received precisely. Preferentially, but not necessarily, the front projection 11d and the rear projections 11e are defined in one and the same part of the casing 11, here represented by the lower part 14 that includes the wall 11c made of material transparent to electromagnetic radiation. It will thus be appreciated that, in this embodiment, two different mutually orthogonal guide systems are provided for insertion and extraction of the casing 11 into/from the seat 9, one including tabs 20 and corresponding recesses 9a', and the other including the projections 9d and 9e, the relief 9b', and the recess 9e'. It will likewise be appreciated that the system including the projections 9d and 9e, the relief 9b', and the recess 9e' represents or advantageously exemplifies a keying or combination for exclusive positioning and/or orientation of the casing 11 in its predetermined position, identified by the seat 9; this keying or combination may, however, be of a different type, as already mentioned.

The embodiment of FIGS. 28-32, with coupling from above of the casing 11 in the seat 9 is advantageous in so far as it enables a more convenient assembly between the parts, for example during assembly of the device, as well as a greater protection of the optical sensor 10, on four sides, in regard to possible leakages of blood coming from the patient. This embodiment, in view of use of the two tabs 20, then enables a more robust engagement and better grip on the two tabs using two fingers during insertion and extraction.

In the embodiments described previously, the optical sensor 10 is basically a sensor of an ON/OFF type, i.e., an optical sensor excited or otherwise following upon reflection or refraction, respectively, of the radiation R. In a different embodiment, operation of a device, which has a structure largely similar to the one described above, could be used in combination with an optical sensor of a different type, and in particular a sensor for light in the visible spectrum designed to detect the colour of the absorbent layer 4, or rather of the upper surface thereof 4b (which, for example, is normally white and becomes red, or in any case darker, following upon absorption of blood).

With reference to the example represented in the drawings so far described, in such a variant embodiment the emitter is replaced by a light source, such as for example a white-light LED, whereas the receiver is replaced by a colour detector, such as an RGB sensor designed to detect a number of colours or a detector selective for the blood-red colour. In such an application, hence, the optical characteristic subject to variation in the case of leakage of blood, that undergoes control by the sensor 10, is a colour. It will be appreciated also that, in such an application, the source of light and the colour detector do not have to be arranged with a clearly specific inclined configuration, as in the case of the components 12-13 of FIGS. 17-18, but may have the respective active optical parts simply facing the layer 4 and/or the point of leakage of the fluid, in the case where the layer 4 is absent.

For instance, in the neutral or anhydrous condition of the layer 4 (i.e., where it is not soaked with liquid), the upper surface thereof 4b has a predefined colour, for example white. The surface 4b is illuminated by the light emitted by the aforesaid source, and the aforesaid colour detector generates an electrical signal that, in the aforesaid neutral condition of the layer 4, has a certain value or is comprised in a given predefined range of values, for example indicating a regular operating condition.

In the case of a leakage, the layer 4 gets soaked with blood. Following upon its diffusion through the layer 4, the blood reaches the upper surface 4b thereof, thereby causing a variation of its colour. in the specific case, the colour of the surface 4b will become darker, passing from light or white to a darker colour, for example, red or in any case the colour of blood.

This variation in colour is detected by the colour detector, with a consequent significant variation of its electrical signal at output, with respect to the value of the signal generated in the neutral condition of the layer 4 or with respect to one of the threshold values of the range of values mentioned previously. Also in this case, the variation of electrical signal is detected via the control electronics of the monitoring unit to which the sensor 10 is connected and is interpreted by the control logic as indicating a leakage of blood in order to govern accordingly activation of the alarm and/or of other devices. In such an embodiment, the presence of the wall 9d is not strictly indispensable, the function of detection surface being fulfilled by the upper surface 4b of the absorbent layer.

Figure 33:
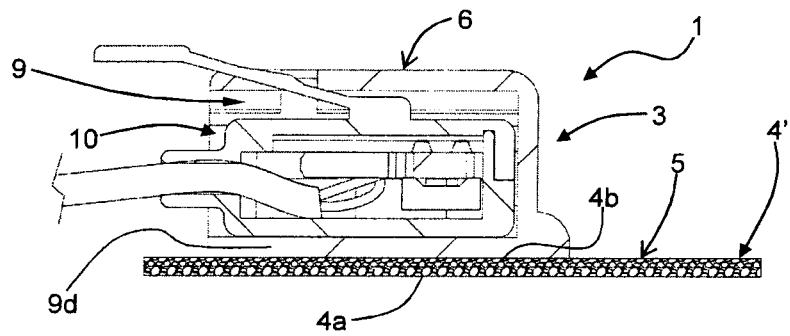
FIGS. 33 and 34 are schematic sections similar to those of FIG. 24, but regarding respective embodiments of a device according to the invention.

The fluid-absorbing layer, when present, can form at least part of a base of the support 2, with the supporting body 3 and the absorbent layer that are constrained together. For instance, FIG. 33 illustrates, via a schematic cross-sectional view, a variant embodiment in which the body 3 basically consists of just the part 6 defining the seat 9 with the corresponding detection wall 9d, underneath which a detection layer 4' is constrained, here more extensive than the layer 4 of the previous figures. In such an embodiment, then, the support is formed as a whole by the body 3 and by the layer 4', with the latter that basically provides the base of the support, even in the absence of a lower seat 5b. In such an embodiment, the layer 4' can also be configured as a fixing element, such as a plaster or a bandage or similar element (fabric, non-woven fabric, cellulose, hydrophilic material, etc.) at least in part adhesive or provided with some other fixing element (such as a mutual engagement element or Velcro at the two ends of the layer 4').

The part 6 can be made of plastic over-moulded on or glued to the layer 4'. FIG. 33 regards a device of the type described with reference to FIGS. 21-24, but the solution can evidently be used also in the presence of the air gap AG, as in FIGS. 1-20.

Figure 34:
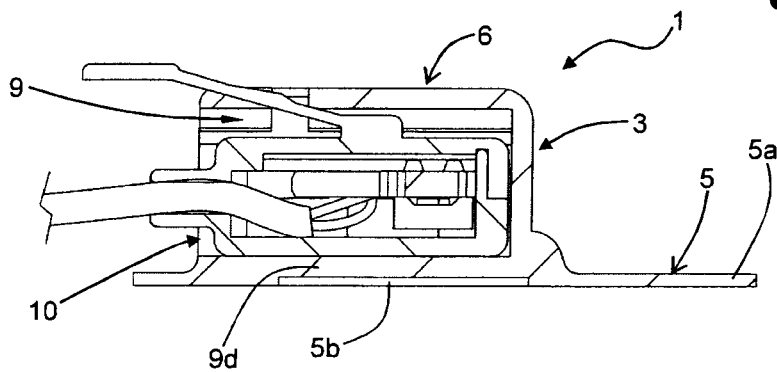

FIG. 34 illustrates, via a schematic cross-sectional view, a further variant embodiment, in which the device is not provided with an absorbent layer. In the example represented, the body 3 of the support 2 includes the base 5, in which a lower cavity or seat 5b is defined, here having a depth smaller than in the embodiments described with reference to FIGS. 1-32, but in any case such as to guarantee an air gap between the lower surface of the wall 9d (i.e., the bottom of the seat 5b) and the skin of the patient. In such an embodiment, the cavity 5b basically provides at least one chamber in which the leakage fluid can be collected until it reaches the lower surface of the wall 9d. Very schematically, in the absence of a leakage of fluid, the interface between the detection surface (lower surface of the wall 9d) and the air is such as to determine reflection of the beam of radiation emitted by the emitter at the receiver of the sensor 10 (basically by total reflection). In the presence of a leakage fluid, this is collected in the cavity 5b until the lower surface of the wall 9d is reached, determining a variation of the optical characteristics of the system, such that there is not sufficient reflection to excite the receiver. A cavity 5b can be constituted by, or be in communication with, at least one channel having micrometric dimensions, with at least one from among width, height, and depth of the channel or chamber comprised between 1 and 999 μm, preferably obtained with techniques of micromoulding of, or on, the body 3 of the support 2. In an embodiment of the type represented in FIG. 34, the body 3 of the support may even be without the base 5, preferably providing other means for fixing to the subject.

Figure 35:
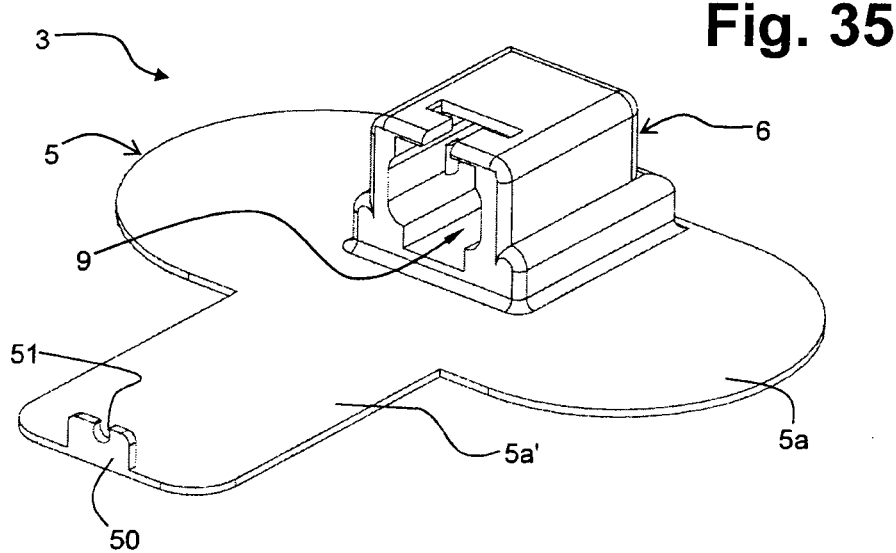
FIG. 35 is a perspective view of a supporting body of a device according to a further variant embodiment of the invention.

FIG. 35 illustrates a further variant embodiment, in which the base 5 of the body 3, and in particular its laminar part 5a, includes a projecting portion 5a', which extends in a position generally aligned with respect to the upper part 6 and/or with respect to the axis of the mouth or front opening of the receiving seat 9 and/or with respect to the direction in which the electric cable 18 extends. In this portion 5a', in particular in a distal region thereof with respect to the part 6, an engagement device 50 is provided, for example including two opposed elastic reliefs, defining a seat for engagement of the cable 18 of the sensor 10, here not represented. In such an embodiment, the portion 5a' is designed to protect further the sensor 10 and/or at least part of the aforesaid cable, at least in the part close to the sensor, i.e., in an area in which the cable itself can be fastened on the body of the patient. Such a solution thus prevents any risk of soiling and contamination of the cable of the optical sensor and/or enables a more convenient or stable fixing of the cable on the subject.

Figure 36:
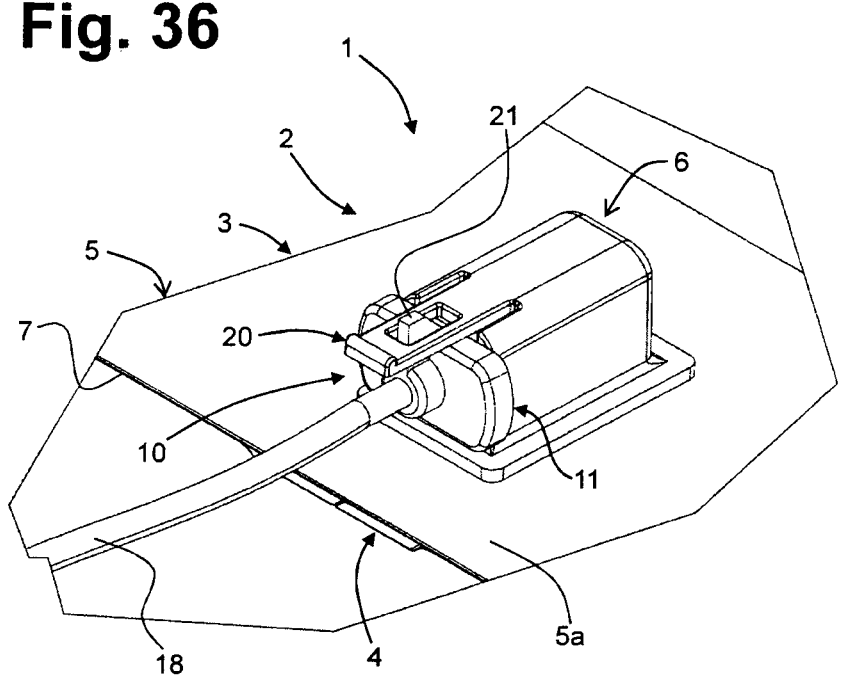
FIGS. 36 and 37 are schematic perspective views, one of which partially sectioned, of a device according to a further variant embodiment of the invention.
Figure 37:
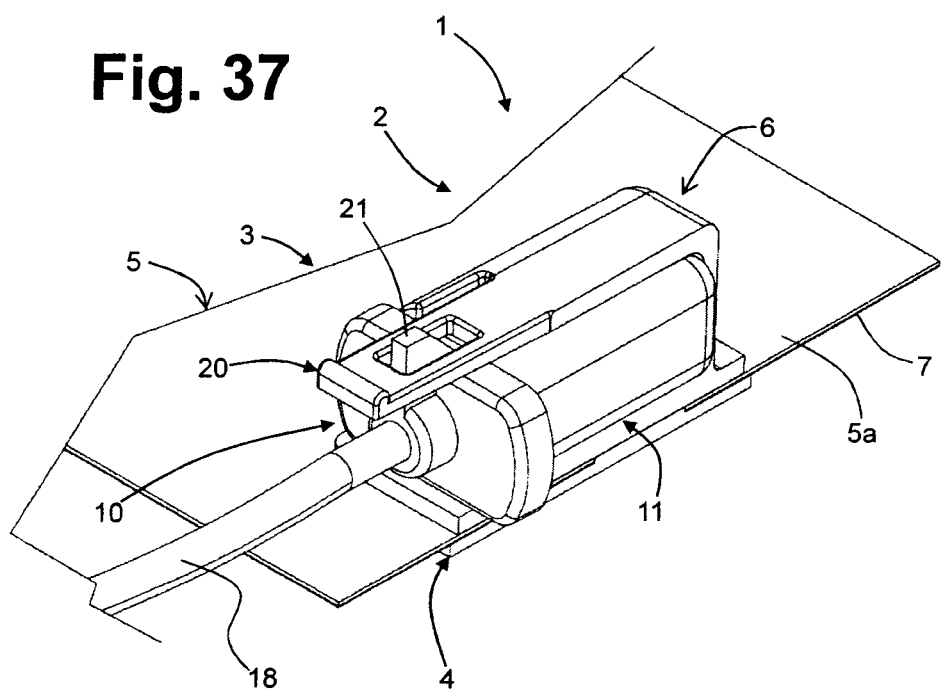

As has already been mentioned, the releasable coupling means between the support and the sensor body can have an arrangement reverse with respect to the one previously exemplified, and hence with a retention element on the casing of the sensor and an engagement element on the support. A possible embodiment in this sense is illustrated in FIGS. 36 and 37, which adopt the same reference numbers as those used in the previous figures. In this case, an engagement element 20 is provided that is associated or made integrally with the body 3, preferably with its upper part 6. In the example, the element 20 includes at least one elastically deformable part, defined within which is at least one engagement seat, that is able to co-operate with at least one retention element 21 that is associated to or made integrally with the casing 11 of the sensor 10. In the example, the retention element 21 is substantially configured as a tooth that can be coupled to the aforesaid engagement seat, the tooth being located in a part of the casing 11, which—in the coupled condition—remains on the outside of the receiving seat that identifies the predetermined position of retention of the casing itself.

From the foregoing description, the characteristics and advantages of the present invention emerge clearly. Of course, without prejudice to the principle of the invention, the details of construction and the embodiments may vary, even significantly, with respect to what has been described and illustrated herein, purely by way of non-limiting example, without thereby departing from the scope of the invention, as defined by the ensuing claims.

The absorbent layer 4 may comprise reacting substances and/or be of the type that undergoes colour change or a change of its optical characteristic when it comes into contact with a fluid, preferably changing colour or optical characteristic in a different way depending on the particular fluid, such as for example a litmus paper. In such an embodiment, the material in question may also be prearranged so as to vary its colour or optical characteristic in the presence of a first fluid, for example the biological or medical fluid of interest, in order to enable detection of leakage by an optical sensor of a predefined type and not change or change differently its own colour or optical characteristic in the presence of a fluid different from the first one, for example water or sweat, so as not to be detectable by the aforesaid optical sensor. The variation of colour or of optical characteristic may thus also be a consequence of a different pH or acidity or basicity of the fluid. Such an embodiment may prove useful in order to prevent any anomalous alarms, for example during excessive sweating of the patient or during washing of the patient, enabling issuing of alarms only following upon a leakage of the fluid of effective interest.

Even though it is preferable, as has already been mentioned, the sensor body does not necessarily have to be configured as casing that encloses completely within it the emitter and the receiver of electromagnetic radiation. As has been mentioned, in possible variant embodiments, the sensor body may include a simple support, such as for example the body of the opto-electronic component designated previously by 17 or 17', which will be provided with the corresponding means for coupling to the support of the device.

The mutual-coupling means, for example the aforementioned combination key and/or the means that fulfil the function thereof, may be envisaged in various differentiated versions, in particular for the case in which different versions of detection devices are provided, each distinguished by an optical sensor and a support of its own, the purpose being to prevent an optical sensor provided for a certain version of device from possibly being erroneously associated to a support provided for a different version of the device. In this perspective, the various versions of the device may also be distinguished by respective colours of the corresponding sensor and support.

In the embodiments previously exemplified, the detection surface of the device consists of, or includes, the lower surface of the wall 9d. In possible variant embodiments, this wall could, however, be omitted, with the function of optical reflection—and hence the function of detection surface—that is fulfilled by the upper surface 4b of the absorbent layer. The presence of the wall 9d must in any case be deemed preferable, in particular for isolating the body of the sensor 10 from the potentially contaminating leakage fluid.

The invention claimed is:

1. A medical fluid-leakage detection device for detecting a leakage fluid on a subject, such as a biological or medical fluid, in particular a leakage of fluid at an area of insertion of a cannula or needle in the subject, the detection device comprising a support, having a supporting body configured for being secured on the subject with a lower face thereof towards the subject, and an optical sensor on the supporting body,
   wherein the supporting body defines a detection surface configured to be reached by leakage fluid and wherein the optical sensor is arranged for detecting a leakage of fluid following upon the presence of leakage fluid on at least part of the detection surface of the supporting body;
   wherein the optical sensor has a sensor body bearing an emitter and a receiver of light radiation, the sensor body being configured as a distinct part with respect to the supporting body and being configured for releasable coupling onto the supporting body;
   wherein the supporting body and the sensor body have respective elements of a coupling arrangement defining a predetermined position of retention of the sensor body on the supporting body, in which position said emitter and receiver are oriented towards the detection surface at a substantially predefined distance with respect to said surface,
   in such a way that a variation of at least one optical characteristic of the detection surface that is induced by the presence of leakage fluid is detectable via the optical sensor,
   and wherein the coupling arrangement is a releasable coupling arrangement, configured for enabling removal of the sensor body from the supporting body; and
   wherein the supporting body comprises at least one from among:
      a fluid-absorbing element, set in such a way that the lower face of the supporting body includes a lower surface of the fluid-absorbing element, the optical sensor being arranged for detecting a leakage of fluid following upon absorption of leakage fluid by the fluid-absorbing element up to an upper surface thereof;
      a wall that is at least in part transparent to light radiation and has a lower surface that extends between the optical sensor and the lower face of the supporting body; and
      a detection surface comprising at least one of an upper surface of a fluid-absorbing element and a lower surface of a wall of the supporting body that is at least in part transparent to light radiation.

2. The medical device according to claim 1, wherein the supporting body defines a receiving seat that identifies said predetermined position of the sensor body and wherein the coupling arrangement is configured for positioning and retention of the sensor body in said predetermined position in the receiving seat, with said emitter and said receiver oriented towards the detection surface.

3. The medical device according to claim 2, wherein the supporting body has a base and an upper body part which rises from the base and in which said receiving seat is defined.

4. The medical device according to claim 3, wherein the base of the supporting body is at least in part substantially laminar, said base and said upper body part being made of a single piece of synthetic material or of a polymeric material.

5. The medical device according to claim 1, wherein the sensor body comprises a sensor casing positioned within which are the emitter and the receiver, the emitter and the receiver being oriented towards a wall of the sensor casing that is at least in part transparent to light radiation and faces the detection surface.

6. The medical device according to claim 1, wherein, in said predetermined position, a first wall of the sensor body that is at least in part transparent to light radiation and a first wall of the supporting body that is at least in part transparent to light radiation face one another, such that a light radiation emitted by said emitter passes through said first wall of the sensor body before reaching said first wall of the supporting body.

7. The medical device according to claim 6, wherein said first wall of the sensor body that is at least in part transparent to light radiation and/or said first wall of the supporting body that is at least in part transparent to light radiation have/has at least one surface with a substantially predetermined roughness, to prevent or reduce undesired light reflection.

8. The medical device according to claim 6, wherein said first wall of the sensor body that is at least in part transparent to light radiation and first said wall of the supporting that is at least in part transparent to light radiation are separated from one another by an air gap.

9. The medical device according to claim 1, wherein the coupling arrangement is configured for enabling removal of the sensor body from said predetermined position or from a corresponding receiving seat defined on the supporting body.

10. The medical device according to claim 1, wherein the optical sensor is a reusable element, and the support is a disposable element.

11. The medical device according to claim 1, wherein the supporting body comprises has a body that defines said detection surface and at least one from among:
   two opposite side walls of a receiving seat between which the sensor body is receivable;
   at least one end wall and two side walls of a receiving seat between which the sensor body is receivable, said at least one end wall being perpendicular to said two side walls; and
   a cavity defining a receiving seat, the cavity having an opening for insertion of the sensor body in a receiving seat, the opening for insertion being generally opposite to a wall of the receiving seat.

12. The medical device according to claim 11, wherein at least two opposite walls of the receiving seat have a shaped surface profile that is substantially complementary to a shaped surface profile of two corresponding opposite side walls of the sensor body.

13. The medical device according to claim 12, wherein said shaped surface profile is designed to form a sliding guide for guiding insertion into, respectively removal from, the receiving seat.

14. The medical device according to claim 1, wherein the coupling arrangement comprises at least one from among:
   a releasable coupling device, including at least one engagement element on one of the sensor body and the supporting body and at least one corresponding retention element on the other one of the supporting body and the sensor body;

sliding and/or positioning guides, which include at least one guide element on the supporting body and at least one corresponding guided element on the sensor body;

positioning elements, which include at least one first part of one of the sensor body and the supporting body and at least one second part of the other one of the sensor body and the supporting body, the at least one first part and the at least one second part co-operating for defining a predetermined retention position;

at least one surface relief of one of the sensor body and the supporting body and at least one corresponding recess of the other one of the sensor body and the supporting body, the at least one relief and the at least one recess being mutually engageable and releasable, respectively, following upon positioning of the sensor body in said predetermined position or its removal from said position, respectively;

a combination key for exclusive coupling and/or positioning of the sensor body in said predetermined position, the key including at least one first key element on the sensor body and at least one second key element on the supporting body uniquely co-operating with the first key element.

15. The medical device according to claim 14, wherein said at least one of the engagement element and the retention element includes at least one elastically deformable part made integrally with at least one of the sensor body and the supporting body and configured for engagement with a corresponding part of the other one of the sensor body and the supporting body.

16. The medical device according to claim 1, wherein the supporting body has a lower cavity, and wherein at least in part housed in said cavity is the fluid-absorbing element with the corresponding upper surface that is substantially in contact with the lower surface of said wall of the supporting body that is at least in part transparent to light radiation.

17. The medical device according to claim 1, wherein the detection surface belongs to a wall of the supporting body configured for isolating the sensor body from the leakage fluid.

18. An optical sensor of a medical fluid-leakage detection device for detecting a leakage fluid on a subject, such as a biological or medical fluid, in particular a leakage of fluid at an area of insertion of a cannula or needle in the subject, the medical detection device being of the type that comprises a support to secure the optical sensor in a working position and which is configured for being fixed on the subject with a lower face thereof towards the subject, the support having a detection surface configured to be reached by leakage fluid, wherein the support has a supporting body comprising at least one from among:
  a fluid-absorbing element, set in such a way that the lower face of the supporting body includes a lower surface of the fluid-absorbing element, the optical sensor being arranged for detecting a leakage of fluid following upon absorption of leakage fluid by the fluid-absorbing element up to an upper surface thereof;
  a wall that is at least in part transparent to light radiation and has a lower surface that extends between the optical sensor and the lower face of the supporting body; and
  a detection surface comprising at least one of an upper surface of a fluid-absorbing element and a lower surface of a wall of the supporting body that is at least in part transparent to light radiation;

wherein the optical sensor has a sensor body or casing bearing an emitter and a receiver of light radiation, the sensor body or casing being configured as a distinct part with respect to the support and being configured for releasable coupling onto the support;

wherein the optical sensor has a coupling arrangement, configured for co-operating with a corresponding coupling arrangement of the support for defining a predetermined position of retention of the sensor body or casing on the support, in which position said emitter and receiver are oriented towards the detection surface of the support, and wherein the coupling arrangement of the optical sensor is releasable from the coupling arrangement of the support to enable removal of the sensor body or casing from the support, the optical sensor being a reusable element.

19. A support of a medical fluid-leakage detection device for detecting a leakage fluid on a subject, such as a biological or medical fluid, in particular a leakage of fluid at an area of insertion of a cannula or needle in the subject, wherein the support is configured for being fixed on the subject with a lower face thereof towards the subject, the detection device being of the type that comprises an optical sensor for detecting a leakage of fluid, having a sensor body configured to be releasably coupled to the support, wherein the support defines a detection surface configured to be reached by leakage fluid, wherein the support comprises a coupling arrangement, configured for co-operating with a corresponding coupling arrangement of the sensor body of the optical sensor, for defining a predetermined position of retention of the sensor body onto the support, in which position an emitter and a receiver of light radiation of the optical sensor are oriented towards the detection surface at a substantially predefined distance from said surface, wherein the support has a supporting body comprising at least one from among:
  a fluid-absorbing element, set in such a way that the lower face of the supporting body includes a lower surface of the fluid-absorbing element, the optical sensor being arranged for detecting a leakage of fluid following upon absorption of leakage fluid by the fluid-absorbing element up to an upper surface thereof;
  a wall that is at least in part transparent to light radiation and has a lower surface that extends between the optical sensor and the lower face of the supporting body; and
  a detection surface comprising at least one of an upper surface of a fluid-absorbing element and a lower surface of a wall of the supporting body that is at least in part transparent to light radiation, and wherein the coupling arrangement of the support is releasable from the coupling arrangement of the sensor body to enable removal of the sensor body from the support, the support being a disposable element.

\* \* \* \* \*